United States Patent [19]

Willms et al.

[11] Patent Number: 5,516,750
[45] Date of Patent: May 14, 1996

[54] SUBSTITUTED ISOXAZOLINES, PROCESS FOR THEIR PREPARATION, COMPOSITION CONTAINING THEM, AND THEIR USE OF SAFENERS

[75] Inventors: Lothar Willms, Hofheim; Klaus Bauer, Hanau; Hermann Bieringer, Eppstein, all of Germany

[73] Assignee: Hoechst Schering AgrEvo GmbH, Berlin, Germany

[21] Appl. No.: 306,110

[22] Filed: Sep. 14, 1994

[30] Foreign Application Priority Data

Sep. 16, 1993 [DE] Germany ............ 43 31 448.1

[51] Int. Cl.$^6$ ............ A01N 43/72; C07D 261/02
[52] U.S. Cl. ............ 504/106; 504/271; 548/247; 548/248; 548/110
[58] Field of Search .............. 548/247, 248, 548/110; 504/271, 106

[56] References Cited

U.S. PATENT DOCUMENTS

| | | | |
|---|---|---|---|
| 3,274,210 | 9/1966 | Fritsch et al. | 260/307 |
| 4,808,750 | 2/1989 | Rogers et al. | 560/62 |
| 4,988,812 | 1/1991 | Kim et al. | 544/263 |
| 5,314,863 | 5/1994 | Löher et al. | 504/100 |
| 5,332,715 | 7/1994 | Löher et al. | 504/193 |

FOREIGN PATENT DOCUMENTS

| | | |
|---|---|---|
| 2089651 | 2/1992 | Canada . |
| 2065983 | 10/1992 | Canada . |
| 2072229 | 12/1992 | Canada . |
| 0509433 | 10/1992 | European Pat. Off. . |
| 0520371 | 12/1992 | European Pat. Off. . |
| WO91/08202 | 6/1991 | WIPO . |
| WO91/18907 | 12/1991 | WIPO . |
| WO92/03053 | 3/1992 | WIPO . |

OTHER PUBLICATIONS

Journal of Indian Chemical Society, Bd. 70, No. 2, Feb. 1993, Calcutta, pp. 134–137, A. Nagarajan et al., entitled "Electron–Impact Mass Spectral Fragmentation Patterns of Isoxazolines".

Chemical Abstracts, vol. 67, No. 21, Nov. 20, 1967, Columbus, Ohio, Abstract No. 100039W, V. A. Tartakovskii et al., entitled "1–3 Dipolar Cycloaddition Unsaturated Compounds", p. 9407.

Chemical Abstracts, vol. 120, No. 11, Mar. 14, 1994, Columbus, Ohio, Abstract No. 134457j, p. 1040.

Angewandte Chemie, International Edition, Band 18, No. 1, 1979, pp. 78–79, Volker Jäger et al., entitled "Ring–Opening of 5–(bromomethyl)–2–isoxazolines to Beta, Gamma–Enoximes", pp. 77–79.

CA86:72623d 3–Isoxazolyl isocyanates. Sumimoto et al., p. 616, 1977.

CA119:219557w Acyclic acids . . . properties Witek et al., p. 341, 1993.

J. Am. Chem. Soc. Bd. 46 (1924), p. 791.

J. Org. Chem. Bd. 25 (1960), p. 1160.

*Primary Examiner*—Joseph K. McKane
*Attorney, Agent, or Firm*—Curtis, Morris & Safford

[57] ABSTRACT

Substituted isoxazolines, process for their preparation, compositions containing them, and their use as safeners.

Compounds of the formula (I) and salts thereof,

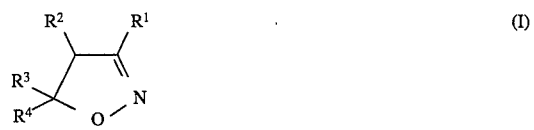

(I)

in which $R^1$ is carboxyl, formyl or another acyl radical or a derivative of the last-mentioned 3 groups, $R^2$ is hydrogen, halogen, $C_1$–$C_{18}$-alkyl, $C_3$–$C_8$-cycloalkyl, $C_2$–$C_8$-alkenyl, $C_2$–$C_8$-alkynyl, $C_1$–$C_{18}$-alkoxy, $C_2$–$C_8$-alkenyloxy, $C_2$–$C_8$-alkynyloxy, $C_1$–$C_{18}$-alkylthio, $C_2$–$C_8$-alkenylthio, each of the last-mentioned 9 radicals in each case being unsubstituted or substituted, or ($C_1$–$C_8$-alkoxy)carbonyl, and $R^3$ and $R^4$ independently of one another are an aliphatic, araliphatic or heteroaraliphatic radical having 1 to 30 carbon atoms which is unsubstituted or substituted by one or more functional groups, or an aromatic or heteroaromatic radical which is unsubstituted or substituted,
are suitable as safenets for pesticides, preferably herbicides, in crop plants. The compounds can be prepared from alkenes (II) and nitrile oxides (III) by the process of claim 6.

13 Claims, No Drawings

SUBSTITUTED ISOXAZOLINES, PROCESS FOR THEIR PREPARATION, COMPOSITION CONTAINING THEM, AND THEIR USE OF SAFENERS

DESCRIPTION

Substituted isoxazolines, process for their preparation, compositions containing them, and their use as safeners.

The invention relates to the technical field of crop protection products, in particular to combinations of active substance and antidote, which are outstandingly suitable for being used against competing harmful plants in crops of useful plants.

When plant treatment products, in particular herbicides, are used, this may result in undesirable damage to the crop plants treated. A large number of herbicides are not fully compatible (selective) with some important crop plants, so that their range of application is limited substantially. This is why they sometimes cannot be used at all, or only at such low application rates that the desired, broad herbicidal activity against the harmful plants is not guaranteed. For example, a large number of herbicides of the substance classes (A) to (K) mentioned below cannot thus be employed in maize, rice or cereals with sufficient selectivity. Phytotoxic side-effects become apparent on the crop plants in particular when these herbicides are applied post-emergence, and it is desirable to avoid or reduce such a phytotoxicity.

It is already known to use herbicides in combination with compounds which reduce the phytotoxicity of the herbicides in crop plants without correspondingly reducing the herbicidal activity against the harmful plants. Such components in combinations are termed safeners or antidotes.

The use of 5-phenylisoxazoline- and 5-phenylisothiazoline- 3-carboxyl derivatives as safenets for herbicides from the series of the carbamates, thiocarbamates, haloacetanilides, phenoxyphenoxyalkanecarboxylic acid derivatives, sulfonylureas and the like has been disclosed in EP-A-509 433 (CA-A-2065983).

EP-A-520371 (CA-A-2072229) mentions, inter alia, 5-alkylisoxazoline- and -isothiazoline-3-carboxyl derivatives as safeners for a range of classes of herbicides.

WO 92/03053 (CA-A-2089651) describes the use of substituted 3-arylisoxazoline- and -isothiazoline-5-carboxyl derivatives as safeners for these herbicides. WO 91/18907 (U.S. Pat. No. 5,332,715) describes silyl-substituted isoxazolines, isoxazoles, isothiazolines and isothiazoles as crop-protecting agents.

Finally, WO 91/08202 (U.S. Pat. No. 5,314,863) describes 5-benzylsubstituted isoxazoline derivatives which have crop-protecting properties.

Surprisingly, it has now been found that compounds from the group of 5,5-disubstituted isoxazoline derivatives of the formula (I) below are outstandingly suitable for protecting crop plants against the damaging effects of aggressive agrochemicals, in particular herbicides.

These isoxazolines, which are suitable for protecting crop plants against harmful effects of aggressive agrochemicals, have the formula (I)

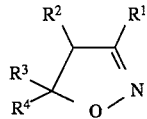

in which
$R^1$ is carboxyl, formyl or another acyl radical, or a derivative of the last-mentioned 3 groups, preferably a radical of the formula

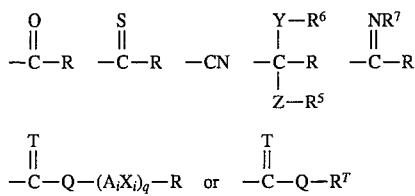

in which R, $R^T$, $R^5$, $R^6$, $R^7$, Y, T, Z, Q, $A_i$, $X_i$ and q are as defined further below, $R^2$ is hydrogen, halogen, $C_1$–$C_{18}$-alkyl, $C_3$–$C_8$-cycloalkyl, $C_2$–$C_8$-alkenyl, $C_2$–$C_8$-alkynyl, $C_1$–$C_{18}$-alkoxy, $C_2$–$C_8$-alkenyloxy, $C_2$–$C_8$-alkynyloxy, $C_1$–$C_{18}$-alkylthio, $C_2$–$C_8$-alkenylthio, each of the last-mentioned 9 radicals being in each case unsubstituted or substituted by one or more radicals selected from the group consisting of halogen, nitro, cyano, $C_1$–$C_4$-alkoxy and ($C_1$–$C_4$-alkoxy)carbonyl, or is ($C_1$–$C_8$-alkoxy)carbonyl, $R^3$ and $R^4$ independently of one another are an aliphatic, araliphatic or heteroaraliphatic radical having 1 to 30 carbon atoms which is unsubstituted or substituted by one or more functional groups, for example a radical $C_1$–$C_{18}$-alkyl, $C_3$–$C_{12}$-cycloalkyl, $C_2$–$C_8$-alkenyl or $C_1$–$C_8$-alkynyl, or an aromatic or heteroaromatic radical which is unsubstituted or substituted, for example an unsubstituted or substituted phenyl, naphthyl or heteroaryl radical, preferably a radical of the formula

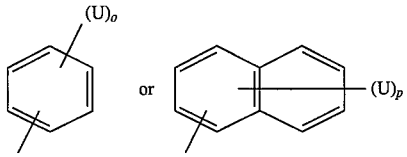

in which
(U) are identical or different radicals which, independently of one another, are hydrogen, halogen, cyano, nitro, amino or $C_1$–$C_8$-haloalkyl, $C_1$–$C_8$-haloalkoxy, $C_1$–$C_8$-alkyl, $C_1$–$C_8$-alkoxy, mono-($C_1$–$C_4$-alkyl)amino, di-($C_1$–C4-alkyl)amino, $C_1$–$C_8$-alkylthio or $C_1$–$C_8$-alkylsulfonyl, each of the last-mentioned 8 radicals being unsubstituted or substituted by one or more, preferably up to three, identical or different substituents selected from the group consisting of halogen, $C_1$–$C_8$-haloalkoxy, nitro, cyano, hydroxyl, $C_1$–$C_8$-alkoxy and an $C_1$–$C_8$-alkoxy group, in which one or more, preferably up to three, $CH_2$ groups are replaced by oxygen, and $C_1$–$C_8$-alkylthio, $C_1$–$C_6$-alkylsulfinyl, $C_1$–$C_6$-alkylsulfonyl, $C_2$–$C_8$-alkenylthio, $C_2$–$C_8$-alkynylthio, $C_2$–$C_8$-alkenyloxy, $C_2$–$C_8$-alkynyloxy, $C_3$–$C_7$-cycloalkyl, $C_3$–$C_7$-cycloalkoxy, mono- and di-($C_1$–$C_4$-alkyl)amino and ($C_1$–$C_6$-alkoxy)carbonyl, preferably hydrogen, halogen, $C_1$–$C_6$-haloalkyl, such as trifluoromethyl, $C_1$–$C_6$-haloalkoxy, such as difluoromethoxy, $C_1$–$C_6$-alkyl, $C_1$–$C_6$-alkoxy, $C_1$–$C_6$-alkylthio, $C_1$–$C_6$-alkylsulfonyl, nitro, amino, ($C_1$–$C_2$-alkyl)amino, di-($C_1$–$C_2$-alkyl)amino or cyano, and o is an integer from 1 to 5, preferably 1 to 3, and p is an integer from 1 to 71 preferably 1 to 3, or, preferably, a monocyclic or bicyclic heteroaryl radical selected from the group consisting of furyl, thienyl, pyrrolyl, pyrazolyl, thiazolyl, oxazolyl, pyridinyl, pyrimidinyl, pyrazinyl, pyridazinyl and quinolinyl, each of which is unsubstituted or substituted by one or more, preferably one to three, of the radicals U mentioned, R is hydrogen or an aliphatic, aromatic, heteroaromatic, araliphatic or heteroaraliphatic radical having 1 to 30 carbon atoms which is unsubstituted or substituted by one or more functional groups, for example R is a radical hydrogen, $C_1$–$C_{18}$-alkyl, $C_3$–$C_{12}$-cycloalkyl, $C_2$–$C_8$-alkenyl or $C_2$–$C_8$-alkynyl, heterocyclyl, phenyl or heteroaryl, each of the last-mentioned 7 radicals independently of one another being unsubstituted or substituted by one or more radicals selected from the group consisting of halogen, cyano, thio, nitro, hydroxyl, $C_1$–$C_8$-alkyl, the latter only in the case of cyclic radicals, $C_1$–$C_8$-haloalkyl, $C_1$–$C_8$-alkoxy, $C_2$–$C_8$-alkenyloxy, $C_2$–$C_8$-alkynyloxy, $C_1$–$C_8$-haloalkoxy, $C_1$–$C_8$-alkylthio, $C_2$–$C_8$-alkenylthio, $C_2$–$C_8$-alkynylthio, $C_3$–$C_7$-cycloalkyl, $C_3$–$C_7$-cycloalkoxy, radicals of the formulae —NR*R** and —CO—NR*R** and —O—CO—NR*R**, where R* and R** in the last-mentioned 3 radicals independently of one another are hydrogen, $C_1$–$C_8$-alkyl, $C_2$–$C_6$-alkenyl, $C_2$–$C_8$-alkynyl, benzyl, phenyl or substituted phenyl, or together with the nitrogen atom are a 3- to 8-membered heterocycle which can additionally contain up to 2 further hetero atoms selected from the group consisting of N, O and S and which can additionally be substituted by $C_1$–$C_4$-alkyl, and also ($C_1$–$C_8$-alkoxy)carbonyl, ($C_1$–$C_8$-alkoxy)thiocarbonyl, ($C_2$–$C_8$-alkenyloxy)carbonyl, ($C_1$–C.-alkylthio) carbonyl, ($C_2$–$C_8$-alkenylthio)carbonyl, ($C_2$–$C_8$-alkynylthio) carbonyl, ($C_2$–$C_8$-alkynyloxy)carbonyl, formyl, ($C_1$–$C_8$-alkyl)carbonyl, ($C_2$–$C_8$-alkenyl)carbonyl, ($C_2$–$C_8$-alkynyl)carbonyl, $C_1$–$C_4$-alkylimino, $C_1$–$C_4$-alkoxyimino, ($C_1$–$C_8$-alkyl)carbonylamino, ($C_2$–$C_8$-alkenyl)carbonylamino, ($C_2$–$C_8$-alkynyl)carbonylamino, ($C_1$–$C_8$-alkoxy)carbonylamino, ($C_2$–$C_8$-alkenyloxy)carbonylamino, ($C_2$–$C_8$-alkynyloxy)carbonylamino, ($C_1$–$C_8$-alkyl)amino-carbonylamino, ($C_1$–$C_6$-alkyl)carbonyloxy, which is unsubstituted or substituted by halogen, $NO_2$. $C_1$–$C_4$-alkoxy or optionally substituted phenyl, and ($C_2$–$C_6$-alkenyl)carbonyloxy, ($C_2$–$C_6$-alkynyl)carbonyloxy, ($C_1$–$C_8$-alkoxy)carbonyloxy, ($C_2$–$C_8$-alkenyloxy)carbonyloxy, ($C_2$–$C_8$-alkynyloxy)carbonyloxy, $C_1$–$C_8$-alkylsulfonyl, phenyl, phenyl-$C_1$–$C_6$-alkoxy, phenyl-($C_1$–$C_6$-alkoxy)carbonyl, phenoxy, phenoxy-$C_1$–$C_6$-alkoxy, phenoxy-($C_1$–$C_6$-alkoxy)carbonyl, phenoxycarbonyl, phenylcarbonyloxy, phenylcarbonylamino, phenyl-($C_1$–$C_6$-alkyl)carbonylamino and phenyl- ($C_1$–$C_6$-alkyl)carbonyloxy, the last-mentioned 11 radicals being unsubstituted or substituted in the phenyl ring by one or more radicals selected from the group consisting of halogen, $C_1$–$C_4$-alkyl, $C_1$–$C_4$-alkoxy, $C_1$–$C_4$-haloalkyl, $C_1$–$C_4$-haloalkoxy and nitro, and radicals of the formulae —SiR'$_3$, —O—SiR'$_3$, (R')$_3$Si—$C_1$–$C_6$-alkoxy, —CO—O—NR'$_2$, —O—N═CR'$_2$, —N═CR'$_2$, O—NR'$_2$, —CH (OR')$_2$ and —O—(CH$_2$)$_m$—CH(OR')$_2$, in which the R' in the formulae mentioned independently of one another are hydrogen, $C_1$–$C_4$-alkyl or phenyl which is unsubstituted or mono- or polysubstituted by radicals selected from the group consisting of halogen, $C_1$–$C_4$-alkyl, $C_1$–$C_4$-alkoxy, $C_1$–$C_4$-haloalkyl, $C_1$–$C_4$-haloalkoxy and nitro, or, in pairs, are a $C_2$–$C_6$-alkylene chain, and m is 0 to 6, and a substituted alkoxy radical of the formula R"OCHR'"CH(OR")—$C_1$–$C_6$-alkoxy, in which the R" independently of one another are $C_1$–$C_4$-alkyl or together are a $C_1$–$C_6$-alkylene group and R'" is hydrogen or $C_1$–$C_4$-alkyl, $R^T$ is a radical of the formula —CO—R, —CS—R, —NR$^f$R$^g$, —N═CR$^h$R$^i$ or SiR$^a$R$^b$R$^c$, R having the meaning mentioned and R$^f$, R$^g$, R$^h$ and R$^i$ independently of one another being hydrogen, $C_1$–$C_4$-alkyl, $C_2$–$C_4$-alkenyl, $C_2$–$C_4$-alkynyl, benzyl, phenyl or substituted phenyl, or R$^f$ and R$^g$ together with the nitrogen atom being a 5- or 6-membered heterocycle which can additionally contain up to 2 further hetero atoms selected from the group consisting of N, O and S and which can additionally be substituted by $C_1$–$C_4$-alkyl, and R$^a$, R$^b$ and R$^c$ independently of one another being $C_1$–$C_4$-alkyl, $C_2$–$C_4$-alkenyl, $C_2$–$C_4$-alkynyl, phenyl or substituted phenyl, Y and Z independently of one another are oxygen, sulfur at its various oxidation levels, preferably S, SO or $SO_2$, or —NR$^3$, R$^e$ being defined analogously to R$^5$ or R$^6$, R$^5$ and R$^6$ are identical or different and, independently of one another, are hydrogen, $C_1$–$C_6$-alkyl, $C_2$–$C_6$-alkenyl, $C_2$–$C_6$-alkynyl or ($C_1$–$C_4$-alkyl)carbonyl, each of the 4 last-mentioned radicals being unsubstituted or substituted by one or more substituents selected from the group consisting of halogen, $C_1$–$C_8$-haloalkoxy, nitro, cyano, hydroxyl, $C_1$–$C_8$-alkoxy and an $C_1$–$C_8$-alkoxy group, in which one or more, preferably up to three, $CH_2$ groups which are not bonded directly to each other are replaced by oxygen, and $C_1$–$C_8$-alkylthio, $C_1$–$C_6$-alkylsulfonyl, $C_2$–$C_8$-alkenylthio, $C_2$–$C_8$-alkynylthio, $C_2$–$C_8$-alkenyloxy, $C_2$–$C_8$-alkynyloxy, $C_3$–$C_7$-cycloalkyl, $C_3$–$C_7$-cycloalkoxy and amino, mono- and di- ($C_1$–$C_4$-alkyl)amino, or formyl or SiR$^a$R$^b$R$^c$, in which R$^a$, R$^b$ and R$^c$ independently of one another are $C_1$–$C_4$-alkyl, $C_2$–$C_4$-alkenyl, $C_2$–$C_4$-alkynyl or unsubstituted or substituted phenyl, or $C_3$–$C_8$-cycloalkyl, $C_3$–$C_8$-cycloalkenyl, heterocyclyl having 3 to 7 ring atoms, aryl, heteroaryl or arylcarbonyl, each of the last-mentioned 6 radicals being unsubstituted or substituted by one or more radicals selected from the group consisting of $C_1$–$C_8$-alkyl, halogen, $C_1$–$C_8$-haloalkoxy, nitro, cyano, hydroxyl, $C_1$–$C_8$-alkoxy and an $C_1$–$C_8$-alkoxy group, in which one or more, preferably up to three, $CH_2$ groups which are not bonded directly to each other are replaced by oxygen, and $C_1$–$C_8$-alkylthio, $C_1$–$C_6$-alkylsulfonyl, $C_2$–$C_8$-alkenylthio, $C_2$–$C_8$-alkynylthio, $C_2$–$C_8$-alkenyloxy, $C_2$–$C_8$-alkynyloxy, $C_3$–$C_7$-cycloalkyl, $C_3$—$C_7$-cycloalkoxy and amino, mono- and di-($C_1$–$C_4$-alkyl)amino, or R$^5$ and R$^6$ together are a $C_2$–$C_4$-alkylene chain or $C_2$–$C_4$-alkenylene chain which is unsubstituted or substituted by 1 or 2 radicals selected from the group consisting of methyl, ethyl, methoxy, ethoxy and halogen, R$^7$ is hydrogen, $C_1$–$C_4$-alkyl, $C_2$–$C_4$-alkenyl, $C_1$–$C_4$-alkynyl, unsubstituted or substituted $C_6$–$C_{12}$-aryl or heteroaryl, benzyl, $C_1$–$C_4$-alkoxy, acyloxy, such as ($C_1$–$C_4$-alkyl)carbonyloxy and unsubstituted or substituted phenylcarbonyloxy, or hydroxyl, —NH—CO—NH$_2$, —NH—CS—NH$_2$, mono- and di- ($C_1$–$C_4$-alkyl)amino, acylamino, ($C_1$–$C_4$-alkyl)sulfonylamino, $C_6$–$C_{12}$-aryloxy, heteroaryloxy, arylsulfonylamino or arylamino, aryl or heteroaryl in the last-mentioned 4 radicals being unsubstituted or substituted by one or more radicals selected from the group consisting of halogen, nitro, $(C_1-C_4)$-alkyl, $(C_1-C_4)$-alkoxy, $(C_1-C_4)$-haloalkyl and $(C_1-C_4)$-haloalkoxy, T is O, S, $NR^8$, N—$OR^8$, or N—O-acyl, Q is O or S, q is an integer from 0 to 4, i is a consecutive number which, in the event that q is not 0, assumes values of all integers from 1 to q, q having the abovementioned meaning, $X_i$ independently of one another are O, S, $NR^9$ or N—$(A_iX_i)_q$—R, $A_i$ independently of one another are unsubstituted or substituted $C_1-C_6$-alkylene, $C_2-C_6$-alkenylene, $C_2-C_6$-alkynylene, $C_3-C_6$-cycloalkylene, $C_3-C_6$-cycloalkenylene, heterocyclylene, arylene or heteroarylene and $R^8$ and $R^9$ independently of one another are H, $C_1-C_4$-alkyl, $C_2-C_4$-alkenyl, $C_2-C_4$-alkynyl, $C_3-C_6$-cycloalkyl, $C_3-C_6$-cycloalkenyl, heterocyclyl, aryl or heteroaryl.

In formula (I) and hereinbelow, the radicals alkyl, alkoxy, haloalkyl, haloalkoxy, alkylamino and alkylthio and the corresponding unsaturated and/or substituted radicals in the carbon skeleton can be in each case straight-chain or branched. Unless specifically indicated, the carbon skeletons having 1 to 4 carbon atoms or, in the case of unsaturated groups, 2 to 4 carbon atoms, are preferred for these radicals. Alkyl radicals, also in the composite meanings such as alkoxy, haloalkyl and the like are, for example, methyl, ethyl, n- or i-propyl, n-, i-, t- or 2-butyl, pentyl radicals, hexyl radicals, such as n-hexyl, i-hexyl and 1,3-dimethylbutyl, heptyl radicals, such as n-heptyl, 1-methylhexyl and 1,4-dimethylpentyl; alkenyl and alkynyl radicals are as defined for the unsaturated radicals which are possible and which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut- 3-en-1-yl and 1-methyl-but-2-en-1-yl; alkynyl is, for example, propargyl, but-2-yn-1-yl, but-3-yn-1-yl, 1-methyl-but-3-yn-1-yl. Halogen is fluorine, chlorine, bromine or iodine, preferably fluorine, chlorine or bromine, in particular fluorine or chlorine. Haloalkyl, -alkenyl and -alkynyl are alkyl, alkenyl or alkynyl, which are partially or fully substituted by halogen, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$. The same applies to haloalkenyl and other radicals which are substituted by halogen.

Aryl is, for example, phenyl, naphthyl, tetrahydronaphthyl, indenyl, indanyl, pentalenyl, fluorenyl and the like, preferably phenyl; aryloxy is preferably the oxy radicals which correspond to the aryl radicals mentioned, in particular phenoxy.

Heteoaryl or heteroaryl in heteroaryloxy is, for example, pyridyl, pyrimidinyl, pyridazinyl, pyrazinyl, thienyl, thiazolyl, oxazolyl, furyl, pyrrolyl, pyrazolyl and imidazolyl, but also bicyclic or polycyclic aromatic or araliphatic compounds, for example quinolinyl, benzoxazolyl and the like.

Substituted aryl or aryloxy, heteroaryl, heteroaryloxy, phenyl, phenoxy, benzyl, benzyloxy or substituted bicyclic radicals having aromatic moieties are, for example, a substituted radical which is derived from the unsubstituted basic skeleton, the substituents being, for example, one or more, preferably 1, 2 or 3, radicals selected from the group consisting of halogen, alkyl, haloalkyl, alkoxy, haloalkoxy, hydroxyl, amino, nitro, cyano, alkoxycarbonyl, alkylcarbonyl, formyl, carbamoyl, mono- and dialkylaminocarbonyl, mono- and dialkylamino, alkylsulfinyl and alkylsulfonyl and, in the case of radicals which have carbon atoms, those having 1 to 4 carbon atoms, in particular 1 or 2, being preferred. As a rule, preferred substituents are selected from the group consisting of halogen, for example fluorine and chlorine, $C_1-C_4$-alkyl, preferably methyl or ethyl, $C_1-C_4$-haloalkyl, preferably trifluoromethyl, $C_1-C_4$-alkoxy, preferably methoxy or ethoxy, $C_1-C_4$-haloalkoxy, nitro and cyano. Particularly preferred are the substituents methyl, methoxy and chlorine.

Optionally substituted phenyl is, for example, phenyl which is unsubstituted or mono- or polysubstituted, preferably up to trisubstituted, by identical or different radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, for example o-, m- and p-tolyl, dimethylphenyl radicals, 2-, 3- and 4-chlorophenyl, 2-, 3- and 4-trifluoro- and -trichlorophenyl, 2,4-, 3,5-, 2,5- and 2,3-dichlorophenyl, and o-, m- and p-methoxyphenyl.

A three- to seven-membered heterocyclic radical as described above is preferably derived from benzene, where at least one CH is replaced by N and/or at least two adjacent CH pairs are replaced by NH, S and/or O. The radical can be benzo-fused. It is optionally partially or fully hydrogenated, in which case it is also termed heterocyclyl. Suitable radicals are, in particular, radicals such as oxiranyl, pyrrolidyl, piperidyl, dioxolanyl, pyrazolyl, morpholyl, furyl, tetrahydrofuryl, indolyl, quinolinyl, pyrimidyl, azepinyl, triazolyl, thienyl and oxazolyl.

Acyl is, for example, formyl, alkylcarbonyl, such as $(C_1-C_4$-alkyl)carbonyl, phenylcarbonyl, it being possible for the phenyl ring to be substituted, for example as shown above in the case of phenyl, or alkyloxycarbonyl, phenyloxycarbonyl, benzyloxycarbonyl, alkylsulfonyl and other radicals of organic acids including carboxyl, formyl and derivatives thereof; carboxyl derivatives are typical acid derivative radicals, such as, for example, salts, esters, thioesters, amides, thioamides, keto acids, amidines and nitriles; formyl derivatives and acyl derivatives are, especially, carbonyl-analog derivatives, such as acetals, thioacetals, thioketals, imines, thioformyl, thioacyl and the like.

Some compounds of the formula (I) contain one or more asymmetric carbon atoms or double bonds which are not separately mentioned in formula (I). The stereoisomers which are possible and which are defined by their specific spatial shape, such as enantiomers, diastereomers, E and Z isomers and their mixtures, however, are all embraced by formula (I).

The compounds of the formula (I) which are derived from carboxylic acids can form salts in which the radical R is replaced by an equivalent of an agriculturally suitable cation. Examples of these salts are metal salts, in particular alkali metal salts (Na,K) or alkaline earth metal salts, but also ammonium salts or salts with organic amines, and salts which contain sulfonium or phosphonium ions as cations.

Particularly suitable as salt formers are metals and organic nitrogen bases, especially quaternary ammonium bases. Possible metals which are suitable for salt formation are alkaline earth metals, such as magnesium or calcium, but especially alkali metals, such as lithium and, in particular, potassium and sodium.

Examples of nitrogen bases which are suitable for salt formation are primary, secondary or tertiary, aliphatic and aromatic amines which are optionally hydroxylated on the hydrocarbon radical, such as methylamine, ethylamine, propylamine, isopropylamine, the four isomeric butylamines, dimethylamine, diethylamine, dipropylamine, diisopropylamine, di-n-butylamine, pyrrolidine, piperidine, morpholine, trimethylamine, triethylamine, tripropylamine, quinuclidine, pyridine, quinoline, isoquinoline, and also methanolamine, ethanolamine, propanolamine, dimethanolamine, diethanolamine or triethanolamine.

Examples of quaternary ammonium bases are tetraalkylammonium cations in which the alkyl radicals independently of one another are straight-chain or branched $C_1$–$C_6$-alkyl groups, such as the tetramethylammoniumcation, the tetraethylammonium cation or the trimethylethylammonium cation, and furthermore the trimethylbenzylammonium cation, the triethylbenzylammonium cation and the trimethyl-2-hydroxyethylammonium cation.

Particularly preferred as salt formers are the ammonium cation and di- as well as trialkylammonium cations in which the alkyl radicals independently of one another are straight-chain or branched ($C_1$–$C_6$)-alkyl groups which are optionally substituted by a hydroxyl group, such as, for example, the dimethylammonium cation, the trimethylammonium cation, the triethylammonium cation, the di(2-hydroxyethyl)ammonium cation and the tri(2-hydroxyethyl)ammonium cation.

Compounds of the formula (I) or salts thereof which are of particular interest are those in which $R^2$ is hydrogen, $C_1$–$C_4$-alkyl, $C_1$–$C_4$-alkoxy or $C_5$–$C_6$-cycloalkyl and at least one of the radicals $R^3$ and $R^4$ is a radical of the formula

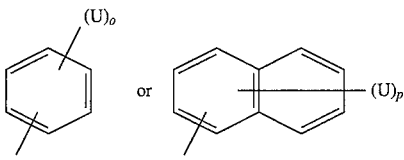

in which (U) are identical or different radicals which, independently of one another, are hydrogen, halogen, such as fluorine, chlorine, bromine and iodine, cyano, nitro, amino, $C_1$–$C_4$-haloalkyl, $C_1$–$C_4$-haloalkoxy, $C_1$–$C_4$-alkyl, $C_1$–$C_4$-alkoxy, mono-($C_1$–$C_4$-alkyl)amino, di-($C_1$–$C_4$-alkyl)amino, $C_1$–$C_4$-alkylthio or $C_1$–$C_4$-alkylsulfonyl, o is an integer from 1 to 3 and p is an integer from 1 to 3, or $R^3$ and $R^4$ independently of one another are a monocyclic or bicyclic heteroaryl radical selected from the group consisting of furyl, thienyl, pyrrolyl, pyrazolyl, thiazolyl, oxazolyl, pyridinyl, pyrimidinyl, pyrazinyl, pyridazinyl and quinolinyl, which is unsubstituted or substituted by one to three of the abovementioned radicals V.

Particularly preferred in the case of the radicals $R^3$ and $R^4$ are identical or different radicals of the formula

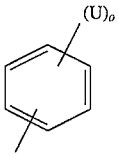

U and o having the abovementioned meanings.

Other compounds of the formula (I) mentioned and salts thereof which are of particular interest are those in which R is hydrogen, $C_1$–$C_8$-alkyl, $C_4$–$C_7$-cycloalkyl, $C_2$–$C_8$-alkenyl or $C_2$–$C_8$-alkynyl, heterocyclyl, phenyl or heteroaryl, each of the last-mentioned 7 radicals independently of one another being unsubstituted or substituted by one or more radicals selected from the group consisting of halogen, cyano, thio, nitro, hydroxyl, $C_1$–$C_4$-alkyl, the latter only in the case of cyclic radicals, $C_1$–$C_4$-haloalkyl, $C_1$–$C_4$-alkoxy, $C_2$–$C_4$-alkenyloxy, $C_2$–$C_4$-alkynyloxy, $C_1$–$C_4$-haloalkoxy, $C_1$–$C_4$-alkylthio, $C_2$–$C_4$-alkenylthio, $C_2$–$C_4$-alkynylthio, $C_5$–$C_6$-cycloalkyl, $C_5$–$C_6$-cycloalkoxy, amino, mono- and di-($C_1$–$C_4$-alkyl)amino, ($C_1$–$C_6$-alkoxy)carbonyl, radicals of the formulae —SiR'$_3$, —O—NR'$_2$, —O—N=CR'$_2$, —N=CR'$_2$, in which the R' in the formulae mentioned independently of one another are hydrogen, $C_1$–$C_2$-alkyl or phenyl or, in pairs, are a $C_2$–$C_5$-alkylene chain, or compounds in which $R^T$ is a radical of the formula —CO—R, —NR$^f$R$^g$ or —N=CR$^h$R$^i$, R, R$^f$, R$^g$, R$^h$ and R$^i$ having the meanings mentioned.

R is preferably hydrogen, $C_1$–$C_8$-alkyl, $C_5$–$C_6$-cycloalkyl, $C_2$–$C_8$-alkenyl or $C_2$–$C_8$-alkynyl, each of the last-mentioned 4 radicals independently of one another being unsubstituted or substituted by one or more radicals selected from the group consisting of halogen, cyano, nitro, $C_1$–$C_4$-alkoxy, $C_2$–$C_4$-alkenyloxy, $C_2$–$C_4$-alkynyloxy, $C_5$–$C_6$-cycloalkyl, $C_5$–$C_6$-cycloalkoxy, mono- and di- ($C_1$–$C_4$-alkyl)amino, radicals of the formulae —SiR'$_3$, —O—N=CR'$_2$, —N=CR'$_2$, in which the R' in the formula mentioned independently of one another are hydrogen, $C_1$–$C_4$-alkyl or phenyl or, in pairs, are a $C_2$–$C_5$-alkylene chain.

$R^T$ is preferably —CO—R, R having the meaning mentioned, or is —NR$^f$R$^g$ or —N=CR$^h$R$^i$, in which R$^f$ and R$^g$ independently of one another are H, $C_1$–$C_2$-alkyl, benzyl or phenyl or, together with the nitrogen atom, are pyrrolidin-1-yl, piperidin-1-yl, morpholin-4-yl, piperazin-1-yl or imidazol-1-yl, or R$^h$ and R$^i$ independently of one another are H, $C_1$–$C_2$-alkyl, benzyl or phenyl.

Other compounds of the formula (I) mentioned and salts thereof which are of particular interest are those in which $R^5$ and $R^6$ are identical or different and independently of one another are hydrogen, $C_1$–$C_4$-alkyl, $C_2$–$C_4$-alkenyl, $C_2$–$C_4$-alkynyl, $C_5$–$C_6$-cycloalkyl or $C_5$–$C_6$-cycloalkenyl, and those compounds in which $R^7$ is hydrogen, $C_1$–$C_4$-alkyl, phenyl, benzyl, hydroxyl, NH—CO—NH$_2$, —NH-aryl or $C_1$–$C_4$-alkoxy.

Other compounds of the formula (I) mentioned and salts thereof which are of particular interest are those in which T is O, S or NR$^8$, preferably O or NR$^8$, Q is O or S, preferably O, q is an integer from 0 to 4, i is a consecutive number which, in the event that q is not 0, assumes values of all integers from 1 to q, q having the abovementioned meaning, $X_i$ independently of one another are O, S, NR$^9$ or N—(A$_i$X$_i$)$_q$—R A$_i$ independently of one another are unsubstituted or substituted $C_1$–$C_4$-alkylene, $C_2$–$C_4$-alkenylene, $C_5$–$C_6$-cycloalkylene, preferably $C_1$–$C_4$-alkylene, R$^8$ and R$^9$ independently of one another are H, $C_1$–$C_4$-alkyl, $C_2$–$C_4$-alkenyl, $C_2$–$C_4$-alkynyl or $C_5$–$C_6$-cycloalkyl.

The invention also relates to a method of protecting crop plants, preferably cereal, rice, maize, soya bean or sugar beet plants, against phytotoxic side-effects of crop protection products, such as herbicides, insecticides and fungicides, which comprises applying an effective amount of at least one compound of the formula (I) or a salt thereof to the plants, the seeds of the plants or the area under cultivation, before, after or simultaneously with the active substances in question.

The invention furthermore relates to the use of compounds of the formula (I) or salts thereof for protecting crop plants against phytotoxic side-effects of crop protection products, such as herbicides, insecticides and fungicides.

The present invention also relates to a process for the preparation of the compound of the formula (I) and salts thereof, which comprises reacting a compound of the formula (II)

$$R^3R^4C=CHR^2 \quad (II)$$

in which $R^2$, $R^3$ and $R^4$ have the meaning given in formula (I), with a nitrile oxide of the formula (III)

$$^{(-)}O-N=^{(+)}C-R^1 \quad (III)$$

in which $R^1$ has the meaning given in formula (I).

The reaction is carried out, for example, in an organic solvent. Preferably suitable as solvents are non-polar to slightly polar organic solvents, for example ethers, such as diethyl ether or tetrahydrofuran (THF).

The starting compounds of the formulae (II) and (III) are known from the literature (cf. J. Org. Chem. 25, 1160 (1960); J. Am. Chem. Soc. 46, 791 (1924) and references cited therein) or can be prepared analogously to the known compounds. The nitrile oxides of the formula (III) as a rule, prepared in situ from 2-halo-2-hydroximinoacetic acid (derivatives) or -ethanal (derivatives) or 2-halo-2-hydroximinoketones with the action of bases, for example organic amine bases, and reacted directly with the compound of the formula (II) which is already present in the reaction mixture. The reaction is preferably carried out at a temperature of −15° C. up to the boiling point of the solvent, in particular at room temperature.

In the text which follows, compounds of the formula (I) also include the salts thereof, unless defined in greater detail.

Compounds of the formula (I) reduce or prevent phytotoxic side-effects of crop protection products, such as herbicides, insecticides and fungicides, which occur when these active substances are used in crops of useful plants, and they can therefore conventionally be termed as antidotes or safeners.

In order to be applied jointly with active substances of crop protection products, the compounds of the formula (I) according to the invention can be applied simultaneously with the active substances or in any desired sequence, and they are then capable of reducing, or completely compensating for, harmful side-effects of these active substances on crop plants without adversely affecting the activity of these active substances against harmful plants or insects or fungal pests. Damage caused by the use of a plurality of crop protection products, for example by a plurality of herbicides or by herbicides in combination with insecticides or fungicides, can also be reduced considerably or compensated for completely. This allows the field of application of conventional crop protection products to be widened quite considerably.

Examples of insecticides which, by themselves or together with herbicides, are capable of causing damage to plants are the following:

Insecticidal preparations, such as organophosphates, for example Terbufos (®Counter), Fonofos (®Dyfonate), Phorate (®Thimet), Chlorpyrifos (®Reldan) and other related active substances; insecticide carbamates, such as, for example carbofuran (®Furadan) and others; and pyrethroid insecticides, such as, for example, Tefluthrin (®Force), deltamethrin (®Decis) and tralomethrin (®Scout) and others; and other insecticidal compositions with a different mechanism of action.

Examples of herbicides whose phytotoxic side-effects on crop plants can be reduced by means of compounds of the formula (I) are, for example, herbicides selected from the group consisting of the carbamates, thiocarbamates, haloacetanilides, substituted phenoxy-, naphthoxy- and phenoxyphenoxycarboxylic acid derivatives, and also heteroaryloxyphenoxyalkanecarboxylic acid derivatives, such as quinolyloxy-, quinoxalyloxy-, pyridyloxy-, benzoxaloxyand benzothiazolyloxyphenoxyalkanecarboxylic acid esters, cyclohexanedione derivatives, imidazolinones, pyrimidyloxypyridinecarboxylic acid derivatives, pyrimidyloxybenzoic acid derivatives, sulfonylureas, triazolopyrimidinesulfonamide derivatives and S-(N-aryl-N-alkylcarbamoylmethyl)dithiophosphoric acid esters. Preferred are the esters and salts of phenoxyphenoxy- and heteroaryloxyphenoxycarboxylic acids, as well as sulfonylureas, imidazolinones and herbicides which, together with ALS inhibitors (acetolactate synthase inhibitors), are employed for broadening the spectrum of action, for example bentszone, cyanazine, atrazine, bromoxynil, dicamba and other foliar-acting herbicides.

Examples of suitable herbicides which can be combined with the safeners according to the invention are:

A) Herbicides of the $(C_1-C_4)$alkyl, $(C_2-C_4)$alkenyl and $(C_3-C_4)$alkynyl phenoxyphenoxy- and heteroaryloxyphenoxycarboxylate type, such as A1) phenoxyphenoxy- and benzyloxyphenoxycarboxylic acid derivatives, for example methyl 2-(4-(2,4-dichlorophenoxy)phenoxy)propionate (diclofop-methyl), methyl 2-(4-(4-bromo-2-chlorophenoxy)phenoxy)propionate (see DE-A-2601548), methyl 2-(4-(4-bromo-2-fluorophenoxy)phenoxy)propionate (see U.S. Pat. No. 4,808,750), methyl 2-(4-(2-chloro-4-trifluoromethylphenoxy)phenoxy)propionate (see DE-A-2433067), methyl 2-(4-(2-fluoro-4-trifluoromethylphenoxy)phenoxy)propionate (see U.S. Pat. No. 4,808,750), methyl 2-(4-(2,4-dichlorobenzyl)phenoxy)propionate (see DE-A-2417487), ethyl 4-(4-(4-trifluoromethylphenoxy)phenoxy)pent-2-enoate, methyl 2-(4-(4-trifluoromethylphenoxy)phenoxy)propionate (see DE-A-2433067), A2) "mononuclear" heteroaryloxyphenoxyalkanecarboxylic acid derivatives, for example ethyl 2-(4-(3,5-dichloropyridyl-2-oxy)phenoxy)propionate (see EP-A-2925), propargyl 2-(4-(3,5-dichloropyridyl-2-oxy)phenoxy)propionate (EP-A-3114), methyl 2-(4-(3-chloro-5-trifluoromethyl-2-pyridyloxy)phenoxy)propionate (see EP-A-3890), ethyl 2-(4-(3-chloro-5-trifluoromethyl-2-pyridyloxy)phenoxy)propionate (see EP-A-3890), propargyl 2-(4-(5-chloro-3-fluoro-2-pyridyloxy)phenoxy)propionate (EP-A-191736), butyl 2-(4-(5-trifluoromethyl-2-pyridyloxy)phenoxy)propionate (fluazifopbutyl), A3) "Binuclear" heteroaryloxyphenoxyalkanecarboxylic acid derivatives, for example methyl and ethyl 2-(4-(6-chloro-2-quinoxalyloxy)phenoxy)propionate (quizalofop-methyl and -ethyl), methyl 2-(4-(6-fluoro-2-quinoxalyloxy)phenoxy)propionate (see J. Pest. Sci. Vol. 10, 61 (1985)), 2-(4-(6-chloro-2-quinoxalyloxy)phenoxy)propionic acid and its 2-isopropylideneaminooxyethyl ester (propaquizafop and its ester), ethyl 2-(4-(6-chlorobenzoxazol-2-yloxy)phenoxy)propionate (fenoxaprop-ethyl), its D(+) isomer (fenoxaprop-P-ethyl) and ethyl 2-(4-(6-chlorobenzthiazol-2-yloxy)phenoxypropionate (see DE-A-2640730), tetrahydrofur-2-ylmethyl 2-(4-(6-chloroquinoxalyloxy)phenoxypropionate (see EP-A 323 727), B) herbicides from the sulfonyl urea series, such as, for example, pyrimidine- or triazinylaminocarbonyl[benzene-, pyridine-, pyrazole-, thiophene- and (alkylsulfonyl)alkylamino] sulfamides. Preferred substituents on the pyrimidine ring or triazine ring are alkoxy, alkyl, haloalkoxy, haloalkyl, halogen or dimethylamino, it being possible for all substituents to be combined independently of one another. Preferred substituents in the benzene, pyridine, pyrazole, thiophene or (alkylsulfonyl)alkylamino moiety are alkyl, alkoxy, halogen, nitro, alkoxycarbonyl, aminocarbonyl, alkylaminocarbonyl, dialkylaminocarbonyl, alkyl, alkylsulfonyl, haloalkoxy, haloalkyl, alkylcarbonyl, alkoxyalkyl, (alkanesulfonyl)alkylamino. Examples of suitable sulfonylureas are B1) phenyl and benzylsulfonylureas and related compounds, for example 1-(2-chlorophenylsulfonyl)-3-(4-methoxy-6-methyl-1,3,5-triazin- 2-yl)urea (chlorosulfuron), 1-(2-ethoxycarbonylphenylsulfonyl)-3-(4-chloro-6-methoxypyrimidin- 2-yl)urea (chlorimuron-ethyl), 1-(2-methoxyphenylsulfonyl)-3-(4-methoxy-6-methyl-1,3,5-triazin- 2-yl)urea (metsulfuron-methyl), 1-(2-chloroethoxy-phenylsulfonyl)-3-(4-methoxy-6-methyl- 1,3,5-triazin-2-yl)urea (triasulfuron), 1-(2-methoxycarbonyl-phenylsulfonyl)-3-(4,6-dimethylpyrimidin- 2-yl)urea (sulfometuron-methyl), 1-(2-methoxycarbonylphenylsulfonyl)-3-(4-methoxy-6-methyl- 1,3,5-triazin-2-yl)-3-methylurea (tribenuronmethyl), 1-(2-methoxycarbonylbenzylsulfonyl)-3-(4,6-dimethoxypyrimidin- 2-yl)urea (bensulfuron-methyl), 1-(2-methoxycarbonylphenylsulfonyl)-3-(4,6-bis-(difluoromethoxy-pyrimidin- 2-yl)urea (primisulfuron-methyl), 3-(4-ethyl-6-methoxy-1,3,5-triazin-2-yl)-1-(2,3-dihydro-1,1-dioxo-2-methylbenzo[b]thiophene-7-sulfonyl)urea (see EP-A-79683), 3-(4-ethoxy-6-ethyl-1,3,5-triazin-2-yl)-1-(2,3-dihydro-1,1-dioxo-2-methylbenzo[b]thiophene-7-sulfonyl)urea (see EP-A-79683), 3-(4-methoxy-6-methyl-1,3,5-triazin-2-yl)-1- (2-methoxycarbonyl- 5-iodophenylsulfonyl)urea (see WO 92/13845)

B2) thienylsulfonylureas, for example 1-(2-methoxycarbonylthiophen- 3-yl)-3-(4-methoxy-6-methyl-1,3,5-triazin-2-yl)urea (thifensulfuron-methyl), B3) pyrazolylsulfonylureas, for example 1-(4-ethoxycarbonyl-1-methylpyrazol-5-yl-sulfonyl)-3-( 4,6-dimethoxypyrimidin-2-yl)urea (pyrazolsulfuronmethyl), methyl 3-chloro-5-(4,6-dimethoxypyrimidin-2-ylcarbamoylsulfamoyl)- 1-methyl-pyrazole-4-carboxylate (see EP 282613), methyl 5-(4,6-dimethylpyrimidin-2-yl)carbamoylsulfamoyl)- 1-(2-pyridyl)pyrazole-4-carboxylate (NC-330, see Brighton Crop Prot. Conference—Weeds—1991, Vol. 1, 45 et seq.), B4) sulfonediamide derivatives, for example 3-(4,6-dimethyoxypyrimidin-2-yl)-1-(N-methyl-N-methylsulfonylaminosulfonyl)urea (amidosulfuron) and structural analogs (see EP-A-0131258 and Z. Pfl. Krankh, Pfl. Schutz 1990, Special Issue XII, 489–497), B5) pyridylsulfonylureas, for example 1-(3-N,N-dimethylaminocarbonylpyridin-2-yl-sulfonyl)-3-( 4,6-dimethoxypyrimidin-2-yl)urea (nicosulfuron), 1-(3-ethylsulfonylpyridin-2-yl-sulfonyl)-3-(4,6-di-methoxy-pyrimidin- 2-yl)urea (DPX-E 9636, see Brighton Crop Prot. Conf.—Weeds—1989, p. 23 et seq.), pyridysulfonylureas as they are described in DE-A-4000503 and DE-A-4030577, preferably those of the formula

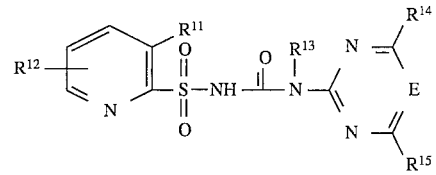

in which

E is CH or N, preferably CH, $R^{11}$ is iodine or $NR^{16}R^{17}$, $R^{12}$ is H, halogen, cyano, $C_1$–$C_3$-alkyl, $C_1$–$C_3$-alkoxy, $C_1$–$C_3$-haloalkyl, $C_1$–$C_3$-haloalkoxy, $C_1$–$C_3$-alkylthio, ($C_1$–$C_3$-alkoxy) –$C_1$–$C_3$-alkyl, ($C_1$–$C_3$-alkoxy) carbonyl, mono- or di- ($C_1$–$C_3$-alkyl)amino, $C_1$–$C_3$-alkylsulfinyl or -sulfonyl, $SO_2$—$NR^aR^b$ or CO—$NR^aR^b$, in particular H, $R^a$ and $R^b$ independently of one another are H, $C_1$–$C_3$-alkyl, $C_1$–$C_3$-alkenyl, $C_1$–$C_3$-alkynyl or together are —$(CH_2)_4$—, —$(CH_2)_5$— or $(CH_2)_2$—O—$(CH_2)_2$—, $R^{13}$ is H or $CH_3$, $R^{14}$ is halogen, $C_1$–$C_2$-alkyl, $C_1$–$C_2$-alkoxy, $C_1$–$C_2$-haloalkyl, preferably $CF_3$, $C_1$–$C_2$-haloalkoxy, preferably $OCHF_2$ or $OCH_2CF_3$, $R^{15}$ is $C_1$–$C_2$-alkyl, $C_1$–$C_2$-haloalkoxy, preferably $OCHF_2$, or $C_1$–$C_2$-alkoxy, and $R^{16}$ is $C_1$–$C_4$-alkyl and $R^{17}$ is $C_1$–$C_4$-alkylsulfonyl or $R^{16}$ and $R^{17}$ together are a chain of the formula —$(CH_2)_3SO_2$— or —$(CH_2)_4SO_2$—, for example 3-(4,6-dimethoxypyrimidin-2-yl)-1-(3-N-methylsulfonyl-N-methylaminopyridin- 2-yl) sulfonylurea, or salts thereof, B6) alkoxyphenoxysulfonylureas as they are described in EP-A-0342569, preferably those of the formula

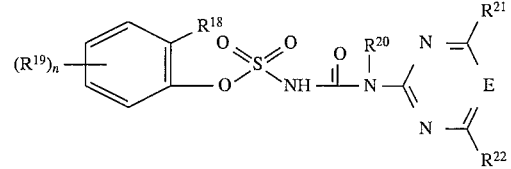

in which

E is CH or N, preferably CH, $R^{18}$ is ethoxy, propoxy or isopropoxy, $R^{19}$ is hydrogen, halogen, $NO_2$, $CF_3$, CN, $C_1$–$C_4$-alkyl, $C_1$–$C_4$-alkoxy, $C_1$–$C_4$-alkylthio or ($C_1$–$C_3$-alkoxy) carbonyl, preferably in the 6-position on the phenyl ring, n is 1, 2 or 3, preferably 1, $R^{20}$ is hydrogen, $C_1$–$C_4$-alkyl or $C_3$–$C_4$-alkenyl, $R^{21}$ and $R^{22}$ independently of one another are halogen, $C_1$–$C_2$-alkyl, $C_1$–$C_2$-alkoxy, $C_1$–$C_2$-haloalkyl, $C_1$–$C_2$-haloalkoxy or ($C_1$–$C_2$-alkoxy)-$C_1$–$C_2$-alkyl, preferably $OCH_2$ or $CH_3$, for example 3- (4,6-dimethoxypyrimidin- 2-yl)-1-(2-ethoxyphenoxy) sulfonyurea, or salts (thereof), and other related sulfonylurea derivatives and mixtures of these, C) chloroacetanilide herbicides, such as N-methoxymethyl-2,6-diethylchloroacetanilide (alachlor), N-(3'-methoxyprop-2'-yl)-2-methyl-6-ethylchloroacetanilide (metolachlor), N-(2,6-dimethyl)-N-(3-methyl-1,2,4-oxadiazol-5-ylmethyl)chloroacetanilide, N-(2,6-dimethylphenyl)-N-(1-pyrazolylmethyl)chloroacetamide (metazachlor), D) thiocarbamates, such as S-ethyl N, N-dipropylthiocarbamate (EPTC) or S-ethyl N,N-diisobutylthiocarbamate (butylate), E) cyclohexanedione derivatives, such as methyl 3-(1-allyloxyiminobutyl)-4-hydroxy-6,6-dimethyl-2-oxocyclohex- 3-enecarboxylate (alloxydim), 2-(1-ethoximinobutyl)-5-(2-ethylthiopropyl)-3-hydroxycyclohex- 2-en-1-one (sethoxydim), 2-(1-ethoximinobutyl)-5-(2-phenylthiopropyl)-3-hydroxycyclohex- 2-en-1-one (cloproxydim), 2-(1-(3-chloroallyloxy)iminobutyl)-5-[2-(ethylthio)propyl] -3-hydroxycyclohex-2-en-1-one, 2-(1-(3-chloroallyloxy)iminopropyl)-5-[2-ethylthio)propyl] -3-hydroxycyclohex-2-en-1-one (clethodim), 2-(1-(ethoxyimino)butyl)-3-hydroxy-5-(thian-3-yl)cyclohex- 2-enone (cycloxydim), or 2-(1-ethoxyiminopropyl)-5-(2,4,6-trimethylphenyl)-3-hydroxycyclohex- 2-ene-1-one (tralkoxydim), F) 2- (4-alkyl-5-oxo-2-imidazolin-2-yl) benzoic acid derivatives or 2- (4-alkyl-5-oxo-2-imidazolin-2-yl)heteroarylcarboxylic acid derivatives, such as, for example, methyl 2- (4-isopropyl-4-methyl-5-oxo-2-imidazolin-2-yl ) 5-methylbenzoate and 2- (4-isopropyl-4-methyl-5-oxo-2-imidazolin-2-yl )-4-methylbenzoic acid (imazamethabenz), 5-ethyl-2- (4-isopropyl-4-methyl-5-oxo-2-imidazolin-2-yl)pyridine- 3-carboxylic acid (imazethapyr), 2- (4-isopropyl-4-methyl-5-oxo-2-imidazolin-2-yl)quinoline- 3-carboxylic acid (imazaquin), 2- (4-isopropyl)-4-methyl-5-oxo-2-imidazolin-2-yl)pyridine- 3-carboxylic acid (imazapyr), 5-methyl-2- (4-isopropyl-4-methyl-5-oxo-2-imidazolin-2-yl)pyridine- 3-carboxylic acid (imazethamethapyr), G) triazolopyrimidinesulfonamide derivatives, for example N-(2,6-difluorophenyl)-7-methyl-1,2,4-triazolo-( 1,5-c)pyrimidine-2-sulfonamide (flumetsulam), N-(2,6-dichloro-3-methylphenyl)-5,7-dimethoxy-1,2,4-triazolo-( 1,5-c)-pyrimidine-2-sulfonamide, N-(2,6-difluorophenyl)-7-fluoro-5-methoxy-1,2,4-triazolo( 1,5-c)-pyrimidine-2-sulfonamide, N-(2,6-dichloro-3-methylphenyl)-7-chloro-5-methoxy-1,2,4-triazolo-( 1,5-c)-pyrimidine-2-sulfonamide, N-(2-chloro-6-methoxycarbonyl)-5,7-dimethyl-1,2,4-triazolo-( 1,5-c)-pyrimidine-2-sulfonamide, (see, for example, EP-A-343 752, U.S. Pat. No. 4,988,812)

H) benzoylcyclohexanedione derivatives, for example 2-(2-chloro-4-methylsulfonylbenzoyl)-cyclohexane-1,3-dione (SC-0051, see EP-A-137963), 2-(2-nitrobenzoyl)-4,4-dimethyl-cyclohexane-1,3-dione (see EP-A-274634), 2-(2-nitro-3-methylsulfonylbenzoyl)-4,4-dimethylcyclohexane- 1,3-dione (see WO-91/13548), J) pyrimidinyloxy pyrimidinecarboxylic acid derivatives or pyrimidinyloxybenzoic acid derivatives, for example benzyl 3-(4,6-dimethoxypyrimidin-2-yl)oxypyridine-2-carboxylate (EP-A-249 707), methyl 3-(4,6-dimethoxypyrimidin-2-yl)oxypyridine-2-carboxylate (EP-A-249 707), 2,6-bis[(4,6-dimethoxypyrimidin-2-yl)oxy]benzoic acid (EP-A 321 846), 1-ethoxycarbonyloxyethyl 2,6-bis[(4,6-dimethoxypyrimidin- 2-yl)oxy]benzoate (EP-A 472 113), and K)S-(N-aryl-N-alkylcarbamoylmethyl)dithiophosphoric acid esters, such as O,O-dimethyl S-[N-(4-chlorophenyl)-N-isopropylcarbamoylmethyl] dithiophosphate (anilofos).

The abovementioned herbicides from groups A to K are known to the expert and described, as a rule, in "The Pesticide Manual", British Crop Protection Council, 9th Edition 1991, or 8th Edition 1987, or in "Agricultural Chemicals Book II, Herbicides", by W. T. Thompson, Thompson Publications, Fresno Calif., USA 1990 or in "Farm Chemicals Handbook '90", Meister Publishing Company, Willoughby Ohio, USA 1990. Imazethamethapyr is known from Weed Techn. 1991, Vol. 5, 430–438.

The herbicidal active substances and the safenero mentioned can be applied together (in the form of a ready-mix or by the tank mix method) or one after the other in any desired sequence. The ratio by weight of safener:herbicide can vary within wide limits and is preferably in a range of 1:10 to 10:1, in particular 1:10 to 5:1. The amounts of herbicide and safener which are ideal in each case depend on the type of the herbicide used or on the safener used as well on the nature of the plant stand to be treated and can be determined in each individual case by suitable preliminary trials. Analogous ratios can be considered when safenero and other active substances of crop protection products, such as insecticides or insecticide/herbicide combinations, are used.

The safeners are mainly employed in cereal crops (wheat, rye, barley, oats), rice, maize, sorghum, but also in cotton and soysbean, preferably in cereals, rice and maize.

A particular advantage of the safenero of the formula (I) according to the invention is to be found when they are combined with herbicides selected from the group consisting of the sulfonylureas and/or imidazolinones, and with herbicides of the phenoxyphenoxy- and heteroaryloxyphenoxyalkanecarboxylic acid derivative type.

Some herbicides of these structural classes cannot be employed specifically in cereal crops and/or maize and rice, or not with sufficient selectivity. Outstanding selectivities can be achieved even with these herbicides in cereals, maize and rice when they are combined with the safenero according to the invention.

Depending on their properties, the safenero of the formula (I) can be used for pre-treating the seed of the crop plant (seed dressing), or they can be incorporated into the seed furrows prior to sowing, or applied together with the herbicide before or after emergence of the plants. Pre-emergence treatment includes both the treatment of the area under cultivation before sowing and treatment of the area under cultivation where seed has been sown, but growth of the crop plants has not yet taken place. The joint use together with the herbicide, in particular by post-emergence methods, is preferred. Tank mixes or ready-mixes can be employed for this purpose.

Depending on the symptoms and the herbicide used, the application rates of safener required can vary within wide limits and are, as a rule, in the range of 0.001 to 5 kg, preferably 0.005 to 0.5 kg, of active substance per hectare.

The present invention therefore also relates to a method of protecting crop plants against phytotoxic side-effects of pesticides, preferably herbicides, which comprises applying an effective amount of a compound of the formula (I) to the plants, seeds of the plants or the area under cultivation before, after or simultaneously with the pesticide or herbicide.

The invention also relates to crop-protecting products which comprise an active substance of the formula (I) and customary formulation auxiliaries, as well as to pesticidal, preferably herbicidal, compositions which comprise an active substance of the formula (I), and a pesticide or herbicide and formulation auxiliaries which are customarily used in the field of crop protection.

The compounds of the formula (I) and their combinations with one or more of the herbicides mentioned can be formulated in a variety of ways, as determined by the biological and/or chemico-physical parameters. The following possibilities are therefore suitable for formulation: wettable powders (WP), emulsifiable concentrates (EC), water-soluble powders (SP), water-soluble concentrates (SL), concentrated emulsions (EW), such as oil-in-water and water-in-oil emulsions, sprayable solutions or emulsions, capsule suspensions (CS), oil-or water-based dispersions (SC), suspoemulsions, suspension concentrates, dusts (DP), oil-miscible solutions (OL), seed-dressing products, granules (GR) in the form of microgranules, spray granules, coated granules and adsorption granules, granules for soil application or broadcasting, water-soluble granules (SG), water-dispersible granules (WG), ULV formulations, microcapsules and waxes.

These individual types of formulations are known in principle and are described, for example, in: Winnacker-Küchler, "Chemische Technologie" [Chemical Technology], Volume 7, C. Hauser Verlag Munich, 4th Edition, 1986; Wade van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives, are also known and described, for example, in: Watkins, "Handbook of Insecticide Dust Diluents and Carriers", 2nd Ed., Darland Books, Caldwell N.J.; H. V. Olphen, "Introduction to Clay Colloid Chemistry", 2nd Ed., J. Wiley & Sons, N.Y.; Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-Active Ethylene Oxide Adducts], Wiss. Verlagsgesell., Stuttgart 1976; Winnacker-Küchler "Chemische Technologie" [Chemical Technology], Volume 7, C. Hauser Verlag Munich, 4th Edition, 1986.

Combinations with other pesticidally active substances, fertilizers and/or growth regulators may also be prepared on the basis of these formulations, for example in the form of a ready-mix or a tank mix.

Wettable powders are preparations which are uniformly dispersible in water and which, besides the active substance, also contain wetting agents, for example polyoxethylated alkylphenols, polyoxethylated fatty alcohols and fatty amines, fatty alcohol polyglycol ether sulfates, alkanesulfonates or alkylarylsulfonates, and dispersing agents, for example sodium lignosulfonate, sodium 2,2'-dinaphthyl-methane-6,6'-disulfonate, sodium dibutylnaphthalenesulfonate or else sodium oleoylmethyltaurate, in addition to a diluent or inert substance.

Emulsifiable concentrates are prepared by dissolving the active substance in an organic solvent, for example butanol, cyclohexanone, dimethylformamide, xylene or else higher-boiling aromatics or hydrocarbons, with addition of one or more emulsifiers. Examples of emulsifiers which can be used are: calcium alkylarylsulfonates, such as calcium dodecylbenzenesulfonate, or non-ionic emulsifiers, such as fatty acid polyglycol esters, alkylaryl polyglycol ethers, fatty alcohol polyglycol ethers, propylene oxide ethylene oxide condensation products (for example block copolymers), alkyl polyethers, sorbitan fatty acid esters, polyoxyethylene sorbitan fatty acid esters or polyoxyethylene sorbitol esters.

Dusts are obtained by grinding the active substance with finely divided solid substances, for example talc, natural clays, such as kaolin, bentonite and pyrophyllite, or diatomaceous earth.

Granules can be prepared either by spraying the active substance onto adsorptive, granulated inert material or by applying active substance concentrates onto the surface of carriers, such as sand, kaolinites or granulated inert material, by means of binders, for example polyvinyl alcohol, sodium polyacrylate or else mineral oils. Suitable active substances can also be granulated in the manner which is conventional for the production of fertilizer granules, if desired in the form of a mixture with fertilizers.

As a rule, the agrochemical preparations contain 0.1 to 99 percent by weight, in particular 0.1 to 95% by weight, of active substances of the formula (I) (antidote) or of the active substance mixture of antidote/herbicide, and 1 to 99.9% by weight, in particular 5 to 99.8% by weight, of a solid or liquid additive, and 0 to 25% by weight, in particular 0.1 to 25% by weight, of a surfactant.

The concentration of active substance in wettable powders is, for example, approximately 10 to 90% by weight, the remainder to 100% being composed of customary formulation components. In the case of emulsifiable concentrates, the concentration of active substance is approximately 1 to 80% by weight of active substances. Formulations in the form of dusts contain approximately 1 to 20% by weight of active substances, sprayable solutions approximately 0.2 to 20% by weight of active substances. In the case of granules, such as water-dispersible granules, the active substance content depends partly on whether the active compound is in liquid or solid form. As a rule, the water-dispersible granules contain between 10 and 90% by weight of active substance.

Besides, the active substance formulations mentioned contain, if appropriate, the adhesives, wetting agents, dispersants, emulsifiers, penetrants, solvents, fillers or carriers which are conventional in each case.

For use, the formulations, which are in commercially available form, are, if appropriate, diluted in the customary manner, for example using water in the case of wettable powders, emulsifiable concentrates, dispersions and water-dispersible granules. Preparations in the form of dusts, granules and sprayable solutions are conventionally not diluted any further with other inert substances before they are used. The application rate of the antidotes required varies with the external conditions such as, inter alia, temperature, humidity, and the nature of the pesticide or herbicide used.

Examples which follow are intended to illustrate the invention:

A. Formulation examples a) A dust is obtained by mixing 10 parts by weight of a compound of the formula (I) or of an active substance mixture of a herbicide and a compound of the formula (I) and 90 parts by weight of talc as inert substance and comminuting the mixture in a hammer mill.

b) A wettable powder which is readily dispersible in water is obtained by mixing 25 parts by weight of a compound of the formula (I) or of an active substance mixture of a herbicide and a safener of the formula (I), 64 parts by weight of kaolin-containing quartz as inert substance, 10 parts by weight of potassium lignosulfonate and 1 part by weight of sodium oleoylmethyltaurate as wetting and dispersing agent, and grinding the mixture in a pinned-disc mill.

c) A dispersion concentrate which is readily dispersible in water is obtained by mixing 20 parts by weight of a compound of the formula (I) or of an active substance mixture of a herbicide and a safener of the formula (I), 6 parts by weight of alkylphenol polyglycol ether ($^R$Triton X 207), 3 parts by weight of isotridecanol polyglycol ether (8 EO) and 71 parts by weight of paraffinic mineral oil (boiling range for example approximately 255° to above 277° C.), and grinding the mixture in a ball mill to a fineness of below 5 microns.

d) An emulsifiable concentrate is obtained from 15 parts by weight of a compound of the formula (I) or an active compound mixture of a herbicide and a safener of the formula (I), 75 parts by weight of cyclohexanone as solvent and 10 parts by weight of ethoxylated nonylphenol as emulsifier.

e) Water-dispersible granules are obtained by mixing

| | |
|---|---|
| 75 parts by weight | of a compound of the formula (I) or of an active substance mixture of a herbicide and a safener of the formula (I), |
| 10 parts by weight | of calcium lignosulfonate, |
| 5 parts by weight | of sodium lauryl sulfate, |
| 3 parts by weight | of polyvinyl alcohol and |
| 7 parts by weight | of kaolin, | grinding the mixture in a pinne-disc mill, and granulating the powder in a fluidized bed by spraying on water as granulation liquid.

f) Water-dispersible granules are also obtained by homogenizing and precomminuting 25 parts by weight of a compound of the formula (I)

| | |
|---|---|
| 25 parts by weight | of a compound of the formula (I) or of an active substance mixture of a herbicide and a safener of the formula (I), |
| 5 parts by weight | of sodium 2,2'-dinaphthylmethane-6,6'-disulfonate, |
| 2 parts by weight | of sodium oleoylmethyltaurate, |
| 1 parts by weight | of polyvinyl alcohol, |
| 17 parts by weight | of calcium carbonate and |
| 50 parts by weight | of water | in a colloid mill, subsequently grinding the mixture in a bead mill, and atomizing and drying the resulting suspension in a spray tower by means of a single-substance nozzle.

B. Preparation examples

1. Ethyl 5,5-diphenyl-2-isoxazoline-3-carboxylate 13.52 g (0.075 mol) of 1,1-diphenylethene and 5.06 g (0.05 mol) of triethylamine are dissolved in 200 ml of ether at 0° C., and 7.58 g (0.05 mol) of ethyl 2-chloro- 2-hydroximinoacetate, dissolved in 100 ml of ether, are subsequently added dropwise in the course of approximately two hours. After stirring has been continued for one hour at room temperature, 100 ml of $H_2O$ are added, and the mixture is subsequently extracted using ether. After drying over a $MgSO_4$, the ether is distilled off and the residue is purified over a silica gel column (eluent: n-heptane:ethyl acetate= 8:2). In this way, 12.7 g (86% of theory) of product of melting point 78° to 81° C. are obtained.

The compounds of Table 1 below are obtained analogously to Example 1 or to the methods described further above.

Abbreviations in Table 1:

Me=methyl

Bu=butyl i-, s-, t-, c-alkyl =iso-, secondary, tertiary or cycloalkyl

M.p.=melting point (in °C.)

TABLE 1

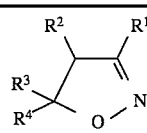

(1)

| Ex. | $R^1$ | $R^2$ | $R^3$ | $R^4$ | M.p. |
|---|---|---|---|---|---|
| 2 | —$COOCH_3$ | H | $C_6H_5$ | $C_6H_5$ | 122–124° C. |
| 3 | —COO-n-$C_3H_7$ | H | $C_6H_5$ | $C_6H_5$ | 64–66° C. |
| 4 | —COO-n-$C_4H_9$ | H | $C_6H_5$ | $C_6H_5$ | oil |
| 5 | —COO-n-$C_5H_{11}$ | H | $C_6H_5$ | $C_6H_5$ | oil |
| 6 | —COO$^-$Na$^+$ | H | $C_6H_5$ | $C_6H_5$ | 210–212° C. (Z) |
| 7 | —COO$^-$N(CH_3)_4$^+$ | H | $C_6H_5$ | $C_6H_5$ | 116° C. (Z) |
| 8 | —$COOCH_2CH_2Cl$ | H | $C_6H_5$ | $C_6H_5$ | 70° C. |
| 9 | —$COOCH_2CH_2OCH_3$ | H | $C_6H_5$ | $C_6H_5$ | oil |
| 10 | —COO-i-$C_3H_7$ | H | $C_6H_5$ | $C_6H_5$ | |
| 11 | —COO-i-$C_4H_9$ | H | $C_6H_5$ | $C_6H_5$ | oil |
| 12 | —COO-s-$C_4H_9$ | H | $C_6H_5$ | $C_6H_5$ | oil |
| 13 | —COO—$C(CH_3)_3$ | H | $C_6H_5$ | $C_6H_5$ | oil |
| 14 | —COO-n-$C_6H_{13}$ | H | $C_6H_5$ | $C_6H_5$ | oil |

TABLE 1-continued

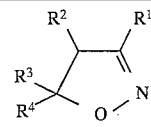

(1)

| Ex. | R¹ | R² | R³ | R⁴ | M.p. |
|---|---|---|---|---|---|
| 15 | —COO-n-$C_8H_{17}$ | H | $C_6H_5$ | $C_6H_5$ | oil |
| 16 | —COOCH$_2$SCH$_3$ | H | $C_6H_5$ | $C_6H_5$ | oil |
| 17 | —COOCH$_2$—CH=CH$_2$ | H | $C_6H_5$ | $C_6H_5$ | 55–57° C. |
| 18 | —COOH | H | $C_6H_5$ | $C_6H_5$ | 85–90° C. |
| 19 | —COOC$_2$H$_5$ | CH$_3$ | $C_6H_5$ | $C_6H_5$ | |
| 20 | —COOC$_2$H$_5$ | —C$_2$H$_5$ | $C_6H_5$ | $C_6H_5$ | |
| 21 | —COO-n-C$_4$H$_9$ | cyclo-C$_3$H$_4$ | $C_6H_5$ | $C_6H_5$ | |
| 22 | —COOCH$_3$ | cyclo-C$_6$H$_{11}$ | $C_6H_5$ | $C_6H_5$ | |
| 23 | —COOC$_2$H$_5$ | —CH$_2$—CH=CH$_2$ | $C_6H_5$ | $C_6H_5$ | 82° C. |
| 24 | —COOC$_2$H$_5$ | —CH$_2$CH$_2$CN | $C_6H_5$ | $C_6H_5$ | |
| 25 | —COO—C$_2$H$_5$ | —COOC$_2$H$_5$ | $C_6H_5$ | $C_6H_5$ | |
| 26 | —COOC$_2$H$_5$ | —OC$_2$H$_5$ | $C_6H_5$ | $C_6H_5$ | |
| 27 | —COOC$_2$H$_5$ | —S—CH$_3$ | $C_6H_5$ | $C_6H_5$ | |
| 28 | —COOCH$_3$ | —CH$_2$COOCH$_3$ | $C_6H_5$ | $C_6H_5$ | |
| 29 | —COOCH$_2$C$_6$H$_5$ | H | $C_6H_5$ | $C_6H_5$ | oil |
| 30 | —COOC$_6$H$_5$ | H | $C_6H_5$ | $C_6H_5$ | |
| 31 | —COOCH$_2$CH$_2$C$_6$H$_5$ | H | $C_6H_5$ | $C_6H_5$ | |
| 32 | —COOC$_2$H$_5$ | H | 2-Cl—C$_6$H$_4$ | $C_6H_5$ | |
| 33 | —COOC$_2$H$_5$ | H | 3-Cl-C$_6$H$_4$ | $C_6H_5$ | oil |
| 34 | —COOC$_2$H$_5$ | H | 4-Cl—C$_6$H$_4$ | $C_6H_5$ | oil |
| 35 | —COOC$_2$H$_5$ | H | 2-F—C$_6$H$_4$ | $C_6H_5$ | |
| 36 | —COOC$_2$H$_5$ | H | 3-F—C$_6$H$_4$ | $C_6H_5$ | |
| 37 | —COOC$_2$H$_5$ | H | 4-F—C$_6$H$_4$ | $C_6H_5$ | oil |
| 38 | —COOC$_2$H$_5$ | H | 4-Cl—C$_6$H$_4$ | 4-Cl—C$_6$H$_4$ | oil |
| 39 | —COOC$_2$H$_5$ | H | 4-Cl—C$_6$H$_4$ | 2-Cl—C$_6$H$_4$ | |
| 40 | —COOC$_2$H$_5$ | H | 4-Cl—C$_6$H$_4$ | 3-Cl—C$_6$H$_4$ | |
| 41 | —COOC$_2$H$_5$ | H | 4-Br—C$_6$H$_4$ | $C_6H_5$ | |
| 42 | —COOC$_2$H$_5$ | H | 4-Br—C$_6$H$_4$ | 4-Cl—C$_6$H$_4$ | oil |
| 43 | —COOC$_2$H$_5$ | H | 4-CF$_3$—C$_6$H$_4$ | $C_6H_5$ | oil |
| 44 | —COOC$_2$H$_5$ | H | 4-CH$_3$—C$_6$H$_4$ | $C_6H_5$ | |
| 45 | —COOC$_2$H$_5$ | H | 4-CH$_3$C$_6$H$_4$ | 4-Cl—C$_6$H$_4$ | oil |
| 46 | —COOC$_2$H$_5$ | H | 2,4-di-Cl—C$_6$H$_3$ | $C_6H_5$ | oil |
| 47 | —COOC$_2$H$_5$ | H | 3,4-di-Cl—C$_6$H$_3$ | $C_6H_5$ | oil |
| 48 | —COOC$_2$H$_5$ | H | 2,5-di-Cl—C$_6$H$_3$ | $C_6H_5$ | |
| 49 | —COOC$_2$H$_5$ | H | 3,5-di-Cl—C$_6$H$_3$ | $C_6H_5$ | |
| 50 | —COOC$_2$H$_5$ | H | 2,6-di-Cl—C$_6$H$_3$ | $C_6H_5$ | |
| 51 | COOC$_2$H$_5$ | H | 4-NO$_2$—C$_6$H$_4$ | $C_6H_5$ | |
| 52 | COOC$_2$H$_5$ | H | 4-CN—C$_6$H$_4$ | $C_6H_5$ | |
| 53 | COOC$_2$H$_5$ | H | 4-COOCH$_3$—C$_6$H$_4$ | $C_6H_5$ | |
| 54 | COOC$_2$H$_5$ | H | 4-OCH$_3$—C$_6$H$_4$ | $C_6H_5$ | 120° C. |
| 55 | COO-n-C$_3$H$_7$ | H | 4-F—C$_6$H$_4$ | $C_6H_5$ | oil |
| 56 | COO-n-C$_3$H$_7$ | H | 4-Cl—C$_6$H$_4$ | $C_6H_5$ | oil |
| 57 | COO-n-C$_4$H$_9$ | H | 4-F—C$_6$H$_4$ | $C_6H_5$ | oil |
| 58 | COO-n-C$_4$H$_9$ | H | 4-Cl—C$_6$H$_4$ | $C_6H_5$ | oil |
| 59 | COO-n-C$_5$H$_{11}$ | H | 4-F—C$_6$H$_4$ | $C_6H_5$ | oil |
| 60 | COO-n-C$_5$H$_{11}$ | H | 4-Cl—C$_6$H$_4$ | $C_6H_5$ | oil |
| 61 | COO-n-C$_6$H$_{13}$ | H | 4-Cl—C$_6$H$_4$ | $C_6H_5$ | oil |
| 62 | COO—CH$_2$CH$_2$Cl | H | 4-Cl—C$_6$H$_4$ | $C_6H_5$ | oil |
| 63 | COO—CH$_2$CH$_2$—OCH$_3$ | H | 4-Cl—C$_6$H$_4$ | $C_6H_5$ | |
| 64 | COOCH(CH$_3$)—CH$_2$(CH$_2$)$_3$CH$_3$ | H | 4-Cl—C$_6$H$_4$ | $C_6H_5$ | |
| 65 | COO—CH$_2$C$_6$H$_5$ | H | 4-Cl—C$_6$H$_4$ | $C_6H_5$ | |
| 66 | COOH | H | 4-Cl—C$_6$H$_4$ | $C_6H_5$ | 86–87° C. |
| 67 | COO$^-$NA$^+$ | H | 4-Cl—C$_6$H$_4$ | $C_6H_5$ | |
| 68 | COO$^-$K+ | H | 4-F—C$_6$H$_4$ | $C_6H_5$ | |
| 69 | COOC$_2$H$_5$ | H | $C_6H_5$ | CH$_3$ | oil |
| 70 | COOCH$_3$ | H | $C_6H_5$ | CH$_3$ | |
| 71 | COOC$_2$H$_5$ | H | $C_6H_5$ | CH(CH$_3$)$_2$ | |
| 72 | COOC$_2$H$_5$ | H | $C_6H_5$ | C(CH$_3$)$_3$ | oil |
| 73 | COOC$_2$H$_5$ | H | 4-Cl—C$_6$H$_4$ | C(CH$_3$)$_3$ | |
| 74 | COO-n-C$_3$H$_7$ | H | $C_6H_5$ | C(CH$_3$)$_3$ | |
| 75 | COO-n-C$_4$H$_9$ | H | $C_6H_5$ | C(CH$_3$)$_3$ | |
| 76 | COO-n-C$_5$H$_{11}$ | H | $C_6H_5$ | C(CH$_3$)$_3$ | |
| 77 | COO-n-C$_6$H$_{13}$ | H | $C_6H_5$ | C(CH$_3$)$_3$ | |
| 78 | COO—CH$_2$CH$_2$OCH$_3$ | H | $C_6H_5$ | C(CH$_3$)$_3$ | |
| 79 | COO—C$_2$H$_5$ | H | $C_6H_5$ | CH$_2$C(CH$_3$)$_3$ | |
| 80 | COO—C$_2$H$_5$ | H | $C_6H_5$ | CH$_2$Si(CH$_3$)$_3$ | |
| 81 | COOC$_2$H$_5$ | H | $C_6H_5$ | cyclo-C$_5$H$_9$ | oil |
| 82 | COOC$_2$H$_5$ | H | $C_6H_5$ | cyclo-C$_6$H$_{11}$ | oil |
| 83 | COOC$_2$H$_5$ | H | $C_6H_5$ | cyclo-C$_3$H$_4$ | oil |

TABLE 1-continued

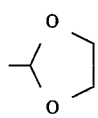

(1)

| Ex. | R¹ | R² | R³ | R⁴ | M.p. |
|---|---|---|---|---|---|
| 84 | COO-n-$C_3H_7$ | H | $C_6H_5$ | cyclo-$C_6H_{11}$ | |
| 85 | COO-n-$C_4H_9$ | H | $C_6H_5$ | cyclo-$C_6H_{11}$ | |
| 86 | COO-n-$C_5H_{11}$ | H | $C_6H_5$ | cyclo-$C_6H_{11}$ | |
| 87 | —$COOC_2H_5$ | H | cyclo-$C_6H_{11}$ | $CH_3$ | |
| 88 | —$COOC_2H_5$ | H | cyclo-$C_6H_{11}$ | $C(CH_3)_3$ | |
| 89 | —$COOC_2H_5$ | H | cyclo-$C_6H_{11}$ | cyclo-$C_6H_{11}$ | |
| 90 | —$COOC_2H_5$ | H | $C_6H_5$ | 2-pyridyl | |
| 91 | —$COOC_2H_5$ | H | $C_6H_5$ | 3-pyridyl | oil |
| 92 | —$COOC_2H_5$ | H | $C_6H_5$ | 4-pyridyl | oil |
| 93 | —$COOC_2H_5$ | H | $C_6H_5$ | 2-thienyl | oil |
| 94 | —$COOC_2H_5$ | H | $C_6H_5$ | 3-thienyl | oil |
| 95 | —$COOC_2H_5$ | H | $C_6H_5$ | 2-Cl-3-pyridyl | oil |
| 96 | —$COOC_2H_5$ | H | $C_6H_5$ | 6-Cl-3-pyridyl | |
| 97 | —$COOC_2H_5$ | H | 4-Cl—$C_6H_4$ | 3-pyridyl | |
| 98 | —$COOC_2H_5$ | H | 3-Cl—$C_6H_4$ | 3-pyridyl | |
| 99 | —$COOC_2H_5$ | H | 2-Cl—$C_6H_4$ | 3-pyridyl | |
| 100 | —COOH | H | $C_6H_5$ | 3-pyridyl | |
| 101 | —$COCH_3$ | H | $C_6H_5$ | $C_6H_5$ | |
| 102 | —$COCH_3$ | H | $C_6H_5$ | cyclo-$C_6H_{11}$ | |
| 103 | —CHO | H | $C_6H_5$ | $C_6H_5$ | |
| 104 | —CHO | H | $C_6H_5$ | cyclo-$C_6H_{11}$ | |
| 105 | —CHO | H | $C_6H_5$ | $C(CH_3)_3$ | |
| 106 | —$CH(OCH_3)_2$ | H | $C_6H_5$ | $C_6H_5$ | |
| 107 | —$CH(OC_2H_5)_2$ | H | $C_6H_5$ | $C_6H_5$ | |
| 108 | 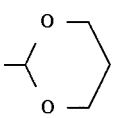 | H | $C_6H_5$ | $C_6H_5$ | |
| 109 | 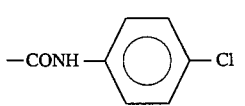 | H | $C_6H_5$ | $C_6H_5$ | |
| 110 | —$C(OCH_3)_2CH_3$ | H | $C_6H_5$ | $C_6H_5$ | |
| 111 | —$COCF_3$ | H | $C_6H_5$ | $C_6H_5$ | |
| 112 | —$COCF_3$ | H | $C_6H_5$ | $C(CH_3)_3$ | |
| 113 | —$COCF_3$ | H | $C_6H_5$ | cyclo-$C_6H_{11}$ | |
| 114 | —$COCCl_3$ | H | $C_6H_5$ | $C_6H_5$ | |
| 115 | —$COCHCl_2$ | H | $C_6H_5$ | $C_6H_5$ | |
| 116 | —$COCHCl_2$ | H | $C_6H_5$ | $C(CH_3)_3$ | |
| 117 | —$COCHCl_2$ | H | $C_6H_5$ | cyclo-$C_6H_{11}$ | |
| 118 | —$COCHF_2$ | H | $C_6H_5$ | $C_6H_5$ | |
| 119 | —$COCHF_2$ | H | $C_6H_5$ | 3-pyridyl | |
| 120 | —COO—CH($CH_3$)$CH_2OCH_3$ | H | $C_6H_5$ | $C_6H_5$ | oil |
| 121 | —COOH | H | 4-F—$C_6H_4$ | 4-F—$C_6H_4$ | 130–134° C. |
| 122 | —COOH | H | 4-F—$C_6H_4$ | $C_6H_5$ | 135–140° C. |
| 123 | —$COOC_2H_5$ | H | —COOCH($CH_3$)—$C_2H_5$ | $C_6H_5$ | oil |
| 124 | —CONH—⟨C₆H₄⟩—Cl | H | —$C_6H_5$ | $C_6H_5$ | 212–215° C. |
| 125 | —$COOC_2H_5$ | H | —$COOC_2H_5$ | $C_6H_5$ | oil |
| 126 | —$COOCH_2COOC_2H_5$ | H | —$C_6H_5$ | $C_6H_5$ | oil |
| 127 | —$CH_2$—C≡CH | H | —$C_6H_5$ | $C_6H_5$ | oil |

TABLE 1-continued $$\begin{array}{c} R^2 \quad R^1 \\ R^3 \diagdown \diagup \\ R^4 \diagup \diagdown O \diagdown N \end{array} \quad (1)$$

| Ex. | R¹ | R² | R³ | R⁴ | M.p. |
|---|---|---|---|---|---|
| 128 | —COO—CH₂—C₆H₄(F) (2-F-benzyl ester) | H | —C₆H₅ | C₆H₅ | oil |
| 129 | —COO—CH(C₂H₅)₂ | H | —C₆H₅ | C₆H₅ | oil |
| 130 | —COO—CH(CH₃)C₂H₅ | H | -4-F—C₆H₄ | C₆H₅ | oil |
| 131 | —COO—CH₂—(tetrahydrofuran-2-yl) | H | —C₆H₅ | C₆H₅ | oil |
| 132 | —COOC₄H₉(n) | H | —C₆H₅ | -2-CH₃C₆H₄ | oil |
| 133 | —COOCH₂—CH₂OC₂H₅ | H | —C₆H₅ | C₆H₅ | oil |
| 134 | —COOC₂H₅ | H | 4-F—C₆H₄ | 4-F—C₆H₄ | oil |
| 135 | —COOC₄H₉(n) | H | 4-F—C₆H₄ | 4-F—C₆H₄ | oil |
| 136 | —CON(CH₃)₂ | H | —C₆H₅ | —C₆H₅ | 105–107° C. |
| 137 | —CONHCH₃ | H | —C₆H₅ | —C₆H₅ | 110–112° C. |
| 138 | —CONH₂ | H | —C₆H₅ | —C₆H₅ | 185–187° C. |
| 139 | —COOCH₂CH₂OH | H | —C₆H₅ | —C₆H₅ | 102–103° C. |
| 140 | —COOC₂H₅ | H | -4-OCH₃—C₆H₄ | -4-F—C₆H₄ | 135–140° C. |
| 141 | CO₂Et | H | 4-NMe₂—C₆H₄ | C₆H₄ | oil |
| 142 | CO₂Et | H | 4-F—C₆H₄ | 2-F—C₆H₄ | oil |
| 143 | CO₂Et | H | 4-Cl—C₆H₄ | 4-t-Bu—C₆H₄ | 86° C. |
| 144 | CO₂Et | H | 4-F—C₆H₄ | 2-Cl—C₆H₄ | oil |
| 145 | CO₂Et | H | 4-F—C₆H₄ | 2,3,4-Cl₃—C₆H₂ | 88° C. |
| 146 | CO₂Et | H | 4-F—C₆H₄ | 3,4-Cl₂—C₆H₃ | oil[1] |
| 147 | CO₂Et | H | 2,4-F₂—C₆H₄ | C₆H₅ | oil |
| 148 | CO₂Et | H | 4-F—C₆H₄ | 2-CH₃—C₆H₄ | oil[2] |
| 149 | CO₂Et | H | 4-F-2-Cl—C₆H₃ | C₆H₅ | oil |
| 150 | CO₂Et | H | 4-Cl-2-F—C₆H₄ | C₆H₅ | oil |

Refractice indices of Ex. 146, 148:
[1] $n_D^{30} = 1,5493$
[2] $n_D^{30} = 1,5530$ C. Biological examples Seeds of wheat, barley or rice are placed in sandy loam soil in plastic pots, and the plants are grown in the greenhouse until they have reached the 3- to 4- leaf stage and then treated post-emergence in succession with the compounds according to the invention and the herbicides. The herbicides and the compounds of the formula (I) are applied in the form of aqueous suspensions or emulsions at an application rate of 300 l of water/ha (converted). 3–4 weeks after the treatment, the plants are scored visually for any type of damage by the herbicides which have been applied, taking into account in particular the extent of sustained growth inhibition. They are assessed in percentages in comparison with untreated controls.

Some test results are compiled in Tables 2, 3 and 4.

TABLE 2

Safener effect in barley

| Product Herbicide/safener | Dosage rate (kg a.i./ha) | Herbicidal activity in % HOVU |
|---|---|---|
|  | 0.2 | 80 |
| H₁ + No. 1 | 0.2 + 1.25 | 60 |
| H₁ + No. 2 | 0.2 + 1.25 | 60 |
| H₁ + No. 6 | 0.2 + 1.25 | 20 |
| H₁ + No. 17 | 0.2 + 1.25 | 20 |
| H₁ + No. 4 | 0.2 + 1.25 | 20 |
| H₁ + No. 3 | 0.2 + 1.25 | 30 |
| H₁ + No. 7 | 0.2 + 1.25 | 37 |

H₁ = Fenoxaprop-P-ethyl
HOVU = *Hordeum vulgare* (Barley)
No. . . . = Safener of Example No. . . . in Section B (Chemical Examples)

TABLE 3

Safener effect in rice

| Product Herbicide/safener | Dosage rate (kg a.i./ha) | Herbicidal activity in % ORSA |
|---|---|---|
| H₁ | 0.3 | 75 |
| H₁ + No. 1 | 0.3 + 1.25 | 60 |
| H₁ + No. 2 | 0.3 + 1.25 | 70 |
| H₁ + No. 6 | 0.3 + 1.25 | 70 |
| H₁ + No. 17 | 0.3 + 1.25 | 70 |
| H₁ + No. 4 | 0.3 + 1.25 | 65 |
| H₁ + No. 3 | 0.3 + 1.25 | 20 |
| H₁ + No. 7 | 0.3 + 1.25 | 70 |

$H_2$ = Fenoxaprop-P-ethyl
ORSA = *Oryza sativa* (rice)

TABLE 4

Safener effect in maize

| Product Herbicide/safener | Dosage rate (kg a.i./ha) | Herbicidal activity in % ZEMV |
|---|---|---|
| H₂ | 0.075 | 70 |
| H₂ + No. 1 | 0.075 + 1.25 | 20 |
| H₂ + No. 2 | 0.075 + 1.25 | 30 |
| H₂ + No. 6 | 0.075 + 1.25 | 50 |
| H₂ + No. 17 | 0.075 + 1.25 | 70 |
| H₂ + No. 4 | 0.075 + 1.25 | 30 |
| H₂ + No. 3 | 0.075 + 1.25 | 40 |
| H₂ + No. 7 | 0.075 + 1.25 | 30 |

$H_2$ = 3-(4,6-dimethoxypyrimidin-2-yl)-1-(3-N-methyl-sulfonyl-N-methylaminopyridin-2-yl)sulfonylurea
ZEMV = *Zea mays* (maize)

EXAMPLE 2

Maize plants are grown in the greenhouse in plastic pots until they have reached the 4-leaf stage or the 6-leaf stage and treated with a tank mix composed of a herbicide and compounds of the formula (I) according to the invention. The preparations are sprayed onto the growing plants at an application rate of 300 l of water/ha. 4 weeks after the treatment, the plants are scored for phytotoxicity, and the extent of the damage is determined by comparison with the untreated control.

The test results, shown in Tables 5 and 6 demonstrate that the compounds according to the invention can prevent damage to plants in a highly efficient manner.

TABLE 5

Effect of the compounds according to the invention on maize plants

| Substances Herbicide/safener | Dosage rate kg AS/ha | | Herbicidal activity in maize (in %) | |
|---|---|---|---|---|
| | | | 4-leaf stage | 6-leaf stage |
| H₂ | 0.200 | | 77 | 83 |
| | 0.100 | | 70 | 73 |
| | 0.050 | | 63 | 60 |
| | 0.025 | | 33 | 40 |
| H₂ + No. 1 | 0.200 | 0.200 | 5 | 10 |
| | 0.100 | 0.100 | 0 | 0 |
| | 0.050 | 0.050 | 0 | 0 |
| | 0.025 | 0.025 | 0 | 0 |
| H₂ + No. 3 | 0.200 | 0.200 | 40 | 0 |
| | 0.100 | 0.100 | 20 | 0 |

TABLE 5-continued

Effect of the compounds according to the invention on maize plants

| Substances Herbicide/safener | Dosage rate kg AS/ha | | Herbicidal activity in maize (in %) | |
|---|---|---|---|---|
| | | | 4-leaf stage | 6-leaf stage |
| | 0.050 | 0.050 | 0 | 0 |
| | 0.025 | 0.025 | 0 | 0 |
| H₂ + No. 17 | 0.200 | 0.200 | 20 | 10 |
| | 0.100 | 0.100 | 10 | 0 |
| | 0.050 | 0.050 | 0 | 0 |
| | 0.025 | 0.025 | 0 | 0 |
| H₂ + No. 6 | 0.200 | 0.200 | 27 | 30 |
| | 0.100 | 0.100 | 7 | 20 |
| | 0.050 | 0.050 | 0 | 10 |
| | 0.025 | 0.025 | 0 | 0 |
| H₂ + No. 7 | 0.200 | 0.200 | 20 | 33 |
| | 0.100 | 0.100 | 0 | 20 |
| | 0.050 | 0.050 | 0 | 0 |
| | 0.025 | 0.025 | 0 | 0 |
| H₂ + No. 4 | 0.200 | 0.200 | 20 | 0 |
| | 0.100 | 0.100 | 0 | 0 |
| | 0.050 | 0.050 | 0 | 0 |
| | 0.025 | 0.025 | 0 | 0 |

$H_2$ = 3-(4,6-dimethoxypyrimidin-2-yl)-1-(3-N-methyl-sulfonyl-N-methylaminopyridin-2-yl)sulfonylurea

TABLE 6

Effect of the compounds according to the invention on maize plants

| Substances Herbicide/safener | Dosage rate kg AS/ha | | Herbicidal activity in maize (in %) | |
|---|---|---|---|---|
| | | | 4-leaf stage | 6-leaf stage |
| H₃ | 0.200 | | 90 | 88 |
| | 0.100 | | 80 | 80 |
| | 0.050 | | 75 | 80 |
| | 0.025 | | 60 | 65 |
| H₃ + No. 3 | 0.200 | 0.200 | 5 | 10 |
| | 0.100 | 0.100 | 0 | 0 |
| | 0.050 | 0.050 | 0 | 0 |
| | 0.025 | 0.025 | 0 | 0 |
| H₃ + No. 4 | 0.200 | 0.200 | 10 | 15 |
| | 0.100 | 0.100 | 0 | 10 |
| | 0.050 | 0.050 | 0 | 0 |
| | 0.025 | 0.025 | 0 | 0 |
| H₃ + No. 7 | 0.200 | 0.200 | 20 | 25 |
| | 0.100 | 0.100 | 0 | 10 |
| | 0.050 | 0.050 | 0 | 0 |
| | 0.025 | 0.025 | 0 | 0 |

$H_3$ = 3-(4-methoxy-6-methyl-1,3,5-triazin-2-yl)-1-(2-methoxycarbonyl)-5-iodophenylsulfonyl)urea

We claim:

1. A compound of the formula (I) or a salt thereof,

(I)

$R^1$ is an acyl radical, $R^2$ is hydrogen, halogen, $C_1$–$C_{18}$-alkyl, $C_3$–$C_8$-cycloalkyl, $C_2$–$C_8$-alkenyl, $C_2$–$C_8$-alkynyl, $C_1$–$C_{18}$-alkoxy, $C_2$–$C_8$-alkenyloxy, $C_2$–$C_8$-alkynyloxy, $C_1$–$C_{18}$-alkylthio, $C_2$–$C_8$-alkenylthio, each of the last-mentioned 9 radicals being in each case unsubstituted or substituted by one or more radicals selected from the group consisting of halogen, nitro, cyano, $C_1$14

$C_4$-alkoxy or ($C_1$–$C_4$-alkoxy) carbonyl, or is ($C_1$–$C_8$-alkoxy) carbonyl, $R^3$ and $R^4$ independently of one another are an aliphatic, araliphatic or heteroaraliphatic radical having 1 to 30 carbon atoms which is unsubstituted or substituted by one or more functional groups, or an aromatic or heteroaromatic radical which is unsubstituted or substituted.

2. A compound of the formula (I) or a salt thereof as claimed in claim 1, $$\underset{R^4}{\overset{R^2}{\underset{R^3}{\diagdown}}}\!\!\!\!\!\!\!\overset{R^1}{\underset{O-N}{\diagup}}\qquad (I)$$

in which $R^1$ is a radical of the formula $$-\overset{O}{\underset{\|}{C}}-R \quad -\overset{S}{\underset{\|}{C}}-R \quad -CN \quad -\overset{Y-R^6}{\underset{Z-R^5}{C}}-R \quad -\overset{NR^7}{\underset{\|}{C}}-R$$

$$-\overset{T}{\underset{\|}{C}}-Q-(A_iX_i)_q-R \quad \text{or} \quad -\overset{T}{\underset{\|}{C}}-Q-R^T$$

in which R, $R^T$, $R^5$, $R^6$, $R^7$, Y, T, Z, Q, $A_i$, $X_i$ and q are as defined further below, $R^2$ is hydrogen, halogen, $C_1$–$C_{18}$-alkyl, $C_3$–$C_8$-cycloalkyl, $C_2$–$C_8$-alkenyl, $C_2$–$C_8$-alkynyl, $C_1$–$C_{18}$-alkoxy, $C_2$–$C_8$-alkenyloxy, $C_2$–$C_8$-alkynyloxy, $C_1$–$C_{18}$-alkylthio, $C_2$–$C_8$-alkenylthio, each of the last-mentioned 9 radicals being in each case unsubstituted or substituted by one or more radicals selected from the group consisting of halogen, nitro, cyano, $C_1$–$C_4$-alkoxy and ($C_1$–$C_4$-alkoxy)carbonyl, or is ($C_1$–$C_8$-alkoxy) carbonyl, $R^3$ and $R^4$ independently of one another are $C_1$–$C_{18}$-alkyl, $C_3$–$C_{12}$-cycloalkyl, $C_2$–$C_8$-alkenyl, $C_2$–$C_8$-alkynyl, or an aromatic or heteroaromatic radical which is unsubstituted or substituted, R is hydrogen or an aliphatic, aromatic, heteroaromatic, araliphatic or heteroaraliphatic radical having 1 to 30 carbon atoms which is unsubstituted or substituted by one or more functional groups, $R^T$ is a radical of the formula —CO—R, —CS—R, —$NR^fR^g$, —N=$CR^hR^i$ or $SiR^aR^bR^c$, R having the meaning mentioned and $R^f$, $R^g$, $R^h$ and $R^i$ independently of one another being hydrogen, $C_1$–$C_4$-alkyl, $C_2$–$C_4$-alkenyl, $C_2$–$C_4$-alkynyl, benzyl, phenyl or substituted phenyl, or $R^f$ and $R^g$ together with the nitrogen atom being a 5- or 6-membered heterocycle which can additionally contain up to 2 further hetero atoms selected from the group consisting of N, O and S and which can additionally be substituted by $C_1$–$C_4$-alkyl, and $R^a$, $R^b$ and $R^c$ independently of one another being $C_1$–$C_4$-alkyl, $C_2$–$C_4$-alkenyl, $C_2$–$C_4$-alkynyl, phenyl or substituted phenyl, Y and Z independently of one another are oxygen, sulfur at its various oxidation levels, or —$NR^e$, $R^e$ being defined analogously to $R^5$ or $R^6$, $R^5$ and $R^6$ are identical or different and, independently of one another, are hydrogen, $C_1$–$C_6$-alkyl, $C_2$–$C_6$-alkenyl, $C_2$–$C_6$-alkynyl or ($C_1$–$C_4$-alkyl) carbonyl, each of the 4 last-mentioned radicals being unsubstituted or substituted by one or more substituents selected from the group consisting of halogen, $C_1$–$C_8$-haloalkoxy, nitro, cyano, hydroxyl, $C_1$–$C_8$-alkoxy and an $C_1$–$C_8$-alkoxy group in which one or more $CH_2$ groups are replaced by oxygen, and $C_1$–$C_8$-alkylthio, $C_1$–$C_6$-alkylsulfonyl, $C_2$–$C_8$-alkenylthio, $C_2$–$C_8$-alkynylthio, $C_2$–$C_8$-alkenyloxy, $C_2$–$C_8$-alkynyloxy, $C_3$–$C_7$-cycloalkyl, $C_3$–$C_7$-cycloalkoxy and amino, mono- and di-(Cl–$C_4$-alkyl)amino, or formyl or $SiR^aR^bR^c$, in which $R^a$, $R^b$ and $R^c$ independently of one another are $C_1$–$C_4$-alkyl, $C_2$–$C_4$-alkenyl, $C_2$–$C_4$-alkynyl or unsubstituted or substituted phenyl, or $C_3$–$C_8$-cycloalkyl, $C_3$–$C_8$-cycloalkenyl, heterocyclyl having 3 to 7 ring atoms, aryl, heteroaryl or arylcarbonyl, each of the last-mentioned 6 radicals being unsubstituted or substituted by one or more radicals selected from the group consisting of $C_1$–$C_8$-alkyl, halogen, $C_1$–$C_8$-haloalkoxy, nitro, cyano, hydroxyl, $C_1$–$C_8$-alkoxy and an $C_1$–$C_8$-alkoxy group, in which one or more $CH_2$ groups which are not bonded directly to each other are replaced by oxygen, and $C_1$–$C_8$-alkylthio, $C_1$–$C_6$-alkyl-sulfonyl, $C_2$–$C_8$-alkenylthio, $C_2$–$C_8$-alkynylthio, $C_2$–$C_8$-alkenyloxy, $C_2$–$C_8$-alkynyloxy, $C_3$–$C_7$-cycloalkyl, $C_3$–$C_7$-cycloalkoxy and amino, mono- and di-($C_1$–$C_4$-alkyl)amino, or $R^5$ and $R^6$ together are a $C_2$–$C_4$-alkylene chain or $C_2$–$C_4$-alkenylene chain which is unsubstituted or substituted by 1 or 2 radicals selected from the group consisting of methyl, ethyl, methoxy, ethoxy and halogen, and also $R^7$ is hydrogen, $C_1$–$C_4$-alkyl, $C_2$–$C_4$-alkenyl, $C_2$–$C_4$-alkynyl, unsubstituted or substituted $C_6$–$C_{12}$-aryl or heteroaryl, benzyl, $C_1$–$C_4$-alkoxy, acyloxy, hydroxyl, —NH—CO—$NH_2$, —NH—CS—$NH_2$, mono- and di-($C_1$–$C_4$-alkyl)-amino, acylamino, ($C_1$–$C_4$-alkyl) sulfonylamino, $C_6$–$C_{12}$-aryloxy, heteroaryloxy, arylsulfonylamino or aryl-amino, in which aryl or heteroaryl in the last-mentioned 4 radicals is unsubstituted or substituted by one or more radicals selected from the group consisting of halogen, nitro, ($C_1$–$C_4$)-alkyl, ($C_1$–$C_4$)-alkoxy, ($C_1$–$C_4$)-haloalkyl and ($C_1$–$C_4$)-haloalkoxy, T is O, S, $NR^8$, N—$OR^8$ or N-O-acyl, Q is O or S, q is an integer from 0 to 4, i is a consecutive number which, in the event that q is not 0, assumes values of all integers from 1 to q, q having the abovementioned meaning, $X_i$ independently of one another are O, S, $NR^9$ or N—$(A_iX_i)_q$—R, $A_i$ independently of one another are unsubstituted or substituted $C_1$–$C_6$-alkylene, $C_1$–$C_6$-alkenylene, $C_1$–$C_6$-alkynylene, $C_3$–$C_6$-cycloalkylene, $C_3$–$C_6$-cycloalkenylene, heterocyclylene, arylene or heteroarylene and $R^8$ and $R^9$ independently of one another are H, $C_1$–$C_4$-alkyl, $C_2$–$C_4$-alkenyl, $C_2$–$C_4$-alkynyl, $C_3$–$C_6$-cycloalkyl, $C_3$–$C_6$-cycloalkenyl, heterocyclyl, aryl or heteroaryl.

3. A compound or a salt thereof as claimed in claim 2, wherein at least one of the radicals $R^3$ and $R^4$ independently of one another are a radical of the formula

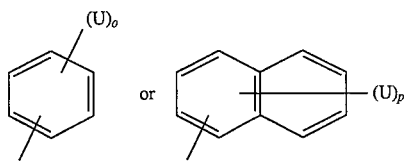

in which
(U) are identical or different radicals which, independently of one another, are hydrogen, halogen, cyano, nitro, amino or $C_1$–$C_8$-haloalkyl, $C_1$–$C_8$-haloalkoxy, $C_1$–$C_8$-alkyl, $C_1$–$C_8$-alkoxy, mono-($C_1$– $C_4$-alkyl)amino, di-($C_1$–$C_4$-alkyl)amino, $C_1$–$C_8$-alkylthio or $C_1$–$C_8$-alkylsulfonyl, each of the last-mentioned 8 radicals being unsubstituted or substituted by one or more identical or different substituents selected from the group consisting of halogen, $C_1$–$C_8$-haloalkoxy, nitro, cyano, hydroxyl, $C_1$–$C_8$-alkoxy and an $C_1$–$C_8$-alkoxy group in which one or more $CH_2$ groups are replaced by oxygen, $C_1$–$C_8$-alkylthio, $C_1$–$C_6$-alkylsulfinyl, $C_1$–$C_6$-alkylsulfonyl, $C_2$–$C_8$-alkenylthio, $C_2$–$C_8$-alkynylthio, $C_2$–$C_8$-alkenyloxy, $C_2$–$C_8$-alkynyloxy, $C_3$– $C_7$-cycloalkyl, $C_3$–$C_7$-cycloalkoxy, mono- and di($C_1$–$C_4$-alkyl)amino and ($C_1$–$C_8$-alkoxy)carbonyl, and o is an integer from 1 to 5 and p is an integer from 1 to 7, or a monocyclic or bicyclic heteroaryl radical selected from the group consisting of furyl, thienyl, pyrrolyl, pyrazolyl, thiazolyl, oxazolyl, pyridinyl, pyrimidinyl, pyrazinyl, pyridazinyl and quinolinyl, each of which is unsubstituted or substituted by one or more of the radicals U mentioned, and $R^1$ is H, $C_1$–$C_{18}$-alkyl, $C_3$–$C_{12}$-cycloalkyl, $C_2$–$C_8$-alkenyl or $C_2$–$C_8$-alkynyl, heterocyclyl, phenyl or heteroaryl, each of the last-mentioned 7 radicals independently of one another being unsubstituted or substituted by one or more radicals selected from the group consisting of halogen, cyano, thio, nitro, hydroxyl, $C_1$–$C_8$-alkyl, the latter only in the case of cyclic radicals, $C_1$–$C_8$-haloalkyl, $C_1$–$C_8$-alkoxy, $C_2$–$C_8$-alkenyloxy, $C_2$–$C_8$-alkynyloxy, $C_1$–$C_8$-haloalkoxy, $C_1$–$C_8$-alkylthio, $C_2$–$C_8$-alkenylthio, $C_2$–$C_8$-alkynylthio, $C_3$–$C_7$-cycloalkyl, $C_3$–$C_7$-cycloalkoxy, radicals of the formulae —NR*R** and —CO—NR*R** and —O—CO—NR*R**, where R* and R** in the last-mentioned 3 radicals independently of one another are hydrogen, $C_1$–$C_8$-alkyl, $C_2$–$C_8$-alkenyl, $C_2$–$C_8$-alkynyl, benzyl, phenyl or substituted phenyl, or together with the nitrogen atom are a 3- to 8-membered heterocycle which can additionally contain up to 2 further hetero atoms selected from the group consisting of N, O and S and which can additionally be substituted by $C_1$–$C_4$-alkyl, and also ($C_1$–$C_8$-alkoxy)carbonyl, ($C_1$–$C_8$-alkoxy)thiocarbonyl, ($C_2$–$C_8$-alkenyloxy)carbonyl, ($C_1$–$C_8$-alkylthio)carbonyl, ($C_2$–$C_8$-alkenylthio)carbonyl, ($C_2$–$C_8$-alkynylthio)carbonyl, ($C_2$–$C_8$-alkynyloxy)carbonyl, formyl, ($C_1$–$C_8$-alkyl)carbonyl, ($C_2$–$C_8$-alkenyl)carbonyl, ($C_2$–$C_8$-alkynyl)carbonyl, $C_1$–$C_4$-alkylimino, $C_1$–$C_4$-alkoxyimino, ($C_1$–$C_8$-alkyl) carbonylamino, ($C_2$–$C_8$-alkenyl)carbonylamino, ($C_2$–$C_8$-alkynyl) carbonylamino, ($C_2$–$C_8$-alkoxy)carbonylamino, ($C_2$–$C_8$-alkenyloxy)carbonylamino, ($C_2$–$C_8$-alkynyloxy)carbonylamino, ($C_1$ –$C_8$-alkyl)amino-carbonyl-amino, ($C_1$–$C_6$-alkyl)carbonyloxy, which is unsubstituted or substituted by halogen, $NO_2$, $C_1$–$C_4$-alkoxy or optionally substituted phenyl, and ($C_2$–$C_6$-alkenyl)carbonyloxy, ($C_2$–$C_6$-alkynyl)-carbonyloxy, ($C_1$–$C_8$-alkoxy)carbonyloxy, ($C_2$–$C_8$-alkenyloxy)carbonyloxy, ($C_2$–$C_8$-alkynyloxy)carbonyloxy, $C_1$–$C_8$-alkylsulfonyl, phenyl, phenyl-$C_1$– $C_6$-alkoxy, phenyl-($C_1$–$C_6$-alkoxy)-carbonyl, phenoxy, phenoxy-$C_1$ –$C_6$-alkoxy, phenoxy- ($C_1$ –$C_6$-alkoxy)carbonyl, phenoxycarbonyl, phenylcarbonyloxy, phenylcarbonyl-amino, phenyl-($C_1$– $C_6$-alkyl) carbonylamino and phenyl-($C_1$–$C_6$-alkyl)carbonyloxy, the last-mentioned 11 radicals being unsubstituted or substituted in the phenyl ring by one or more radicals selected from the group consisting of halogen, $C_1$–$C_4$-alkyl, $C_1$–$C_4$-alkoxy, $C_1$–$C_4$-haloalkyl, $C_1$–$C_4$-haloalkoxy and nitro, and radicals of the formulae —SiR'$_3$, —O—SiR'$_3$, (R')$_3$Si-$C_1$–$C_6$-alkoxy, —CO—O—NR'$_2$, —O—N=CR'$_2$, N=CR'$_2$, —O—NR'$_2$, —CH(OR')$_2$ and —O—(CH$_2$)$_m$—CH(OR')$_2$, in which the R' in the formulae mentioned independently of one another are hydrogen, $C_1$–$C_4$-alkyl or phenyl which is unsubstituted or mono- or polysubstituted by radicals selected from the group consisting of halogen, $C_1$–$C_4$-alkyl, $C_1$–$C_4$-alkoxy, $C_1$–$C_4$-haloalkyl, $C_1$–$C_4$-haloalkoxy and nitro, or, in pairs, are a $C_2$–$C_6$-alkylene chain, and m is 0 to 6, and a substituted alkoxy radical of the formula R"OCHR"'CH (OR")-$C_1$–$C_6$-alkoxy, in which the R" independently of one another are $C_1$–$C_4$-alkyl or together are a $C_1$–$C_6$-alkylene group and R"' is hydrogen or $C_1$–$C_4$-alkyl.

4. A compound or a salt thereof as claimed in claim 2, wherein $R^2$ is hydrogen, $C_1$–$C_4$-alkyl, $C_1$–$C_4$-alkoxy or $C_5$–$C_6$-cycloalkyl and at least one of the radicals $R^3$ and $R^4$ is a radical of the formula

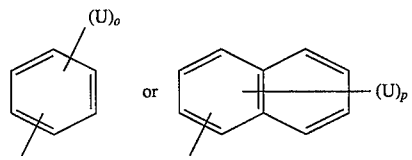

in which
(U) are identical or different radicals which, independently of one another, are hydrogen, halogen, such as fluorine, chlorine, bromine and iodine, cyano, nitro, amino, $C_1$–$C_4$-haloalkyl, $C_1$–$C_4$-haloalkoxy, $C_1$–$C_4$-alkyl, $C_1$–$C_4$-alkoxy, mono-($C_1$–$C_4$-alkyl)amino, di-($C_1$–$C_4$-alkyl)amino, $C_1$–$C_4$-alkylthio or $C_1$–$C_4$-alkylsulfonyl, o is an integer from 1 to 3 and p is an integer from 1 to 3, or one of the radicals $R^3$ and $R^4$ independently of one another are a monocyclic or bicyclic heteroaryl radical selected from the group consisting of furyl, thienyl, pyrrolyl, pyrazolyl, thiazolyl, oxazolyl, pyridinyl, pyrimidinyl, pyrazinyl, pyridazinyl and quinolinyl, which is unsubstituted or substituted by one to three of the abovementioned radicals U.

5. A compound or a salt thereof as claimed in claim 2, wherein $R^3$ and $R^4$ independently of one another are identical or different radicals of the formula

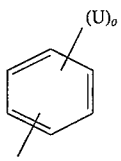

and

R is hydrogen, $C_1$–$C_8$-alkyl, $C_4$–$C_7$-cycloalkyl, $C_2$–$C_8$-alkenyl or $C_2$–$C_8$-alkynyl, heterocyclyl, phenyl or heteroaryl, each of the last-mentioned 7 radicals independently of one another being unsubstituted or substituted by one or more radicals selected from the group consisting of halogen, cyano, thio, nitro, hydroxyl, $C_1$–$C_4$-alkyl, the latter only in the case of cyclic radicals, $C_1$–$C_4$-haloalkyl, $C_1$–$C_4$-alkoxy, $C_2$–$C_4$-alkenyloxy, $C_2$–$C_4$-alkynyloxy, $C_1$–$C_4$-haloalkoxy, $C_1$–$C_4$-alkylthio, $C_2$–$C_4$-alkenylthio, $C_2$–$C_4$-alkynylthio, $C_5$–$C_6$-cycloalkyl, $C_5$–$C_6$-cycloalkoxy, amino, mono- and di-($C_1$–$C_4$-alkyl)amino, ($C_1$–$C_6$-alkoxy)carbonyl, radicals of the formulae —SiR'$_3$, —O—NR'$_2$, —O—N=CR'$_2$, —N=CR'$_2$, in which the R' in the formulae mentioned independently of one another are hydrogen, $C_1$–$C_2$-alkyl or phenyl or, in pairs, are a $C_2$–$C_5$-alkylene chain, and $R^T$ is a radical of the formula —CO—R, —NR$^f$R$^g$ or —N=CR$^h$R$^i$.

6. A crop protection product, which comprises, a compound of the formula (I) or a salt thereof as claimed in claim 1 as crop-plant-protecting component as well as formulation auxiliaries which are customary in crop protection.

7. A crop protection product, which comprises, a compound of the formula (I) or a salt thereof as claimed in claim 2 as crop-plant-protecting component as well as formulation auxiliaries which are customary in crop protection.

8. A crop protection product which comprises at least one pesticide and, as safener, at least one compound of formula (I) or a salt thereof as claimed in claim 1.

9. A method of protecting crop plants against phytotoxic side-effects of active substance in crop protection products (pesticides), which comprises applying an effective amount of at least one of the compounds of the formula (I) or a salt thereof as claimed in claim 1 to the plants, the seeds of the plants or the area under cultivation before, after or simultaneously with the in question pesticide.

10. A compound of formula (I), or a salt thereof, as claimed in claim 1 wherein $R^1$ is carboxyl, formyl, alkylcarbonyl, phenylcarbonyl which is unsubstituted or substituted at the phenyl ring, alkylsulfonyl, or CN or the functional group of carboxylic esters, thioesters, amides, thioamides, amidines, acetals, thioketals, imines, or is thioformyl.

11. A compound of formula (I), or a salt thereof, as claimed in claim 10 wherein $R^3$ and $R^4$ independently of one another are $C_1$–$C_{18}$-alkyl, $C_3$–$C_{12}$-cycloalkyl, $C_2$–$C_8$-alkenyl, $C_2$–$C_8$-alkynyl, or are $C_1$–$C_4$-alkoxycarbonyl or trimethylsilymethyl or are an aromatic or heteroaromatic radical which is unsubstituted or substituted.

12. A compound of formula (I), or a salt thereof, as claimed in claim 1 wherein $R^1$ is carboxyl, formyl, $C_1$–$C_4$-alkylcarbonyl, phenylcarbonyl which is unsubstituted or substituted at the phenyl ring, or is $C_1$–$C_4$-alkoxycarbonyl, phenoxycarbonyl, benzyloxycarbonyl, $C_1$–$C_4$-alkylsulfonyl, or CN or aminocarbonyl, imino group or an acetal group, and $R^3$ and $R^4$ independently of one another are $C_1$–$C_{18}$-alkyl, $C_3$–$C_{12}$-cycloalkyl, $C_2$–$C_8$-alkenyl, $C_2$–$C_8$-alkynyl, or are an aromatic or heteroaromatic radical which is unsubstituted or substituted.

13. A compound of formula (I), or a salt thereof, as claimed in claim 5 wherein $R^1$ is a group of the formula —CO—OR, R is $C_1$–$C_4$-alkyl, and $R^2$ is hydrogen.

* * * * *